(12) United States Patent
Baetz et al.

(10) Patent No.: US 11,555,210 B2
(45) Date of Patent: Jan. 17, 2023

(54) MICROBE HAVING INCREASED TOLERANCE TO PHENOLIC FERMENTATION INHIBITORS

(71) Applicant: University of Ottawa, Ottawa (CA)

(72) Inventors: Kristin Baetz, Ottawa (CA); Eugene Fletcher, Ottawa (CA)

( * ) Notice: Subject to any disclaimer, the term of this patent is extended or adjusted under 35 U.S.C. 154(b) by 70 days.

(21) Appl. No.: 17/285,654

(22) PCT Filed: Oct. 15, 2019

(86) PCT No.: PCT/CA2019/000143
§ 371 (c)(1),
(2) Date: Apr. 15, 2021

(87) PCT Pub. No.: WO2020/077433
PCT Pub. Date: Apr. 23, 2020

(65) Prior Publication Data
US 2021/0395787 A1    Dec. 23, 2021

Related U.S. Application Data

(60) Provisional application No. 62/746,178, filed on Oct. 16, 2018.

(51) Int. Cl.
C12P 7/24    (2006.01)
C12N 1/18    (2006.01)

(52) U.S. Cl.
CPC ............... *C12P 7/24* (2013.01); *C12N 1/185* (2021.05)

(58) Field of Classification Search
CPC .. C12P 7/24; C12N 9/80; C12N 15/81; C12N 1/18
See application file for complete search history.

(56) References Cited

FOREIGN PATENT DOCUMENTS

WO    2018083301 A2    5/2018

OTHER PUBLICATIONS

International Search Report for corresponding PCT Application No. PCT/CA2019/000143.
Liu, "Molecular mechanisms of yeast tolerance and in situ detoxification oflignocellulose hydrolysates". Applied Microbiology and Biotechnology, Mar. 5, 2011 (Mar. 5, 2011), vol. 90, pp. 809-825, ISSN 1432-0614 [online].
Wogulis et al., "Identification offormyl kynurenineformamidase and kynurenine aminotransferase from *Saccharomyces cerevisiae* using crystallographic, bioinformatic and biochemical evidence". Biochemistry, 2008, vol. 47, pp. 1608-1621, ISSN 1520-4995 [online].
Fletcher et al., "Yeast chemogenomic screen identifies distinct metabolic pathways required to tolerate exposure to phenolic fermentation inhibitorsferulic acid, 4-hydroxybenzoic acid and coniferyl aldehyde". Metabolic Engineering, Nov. 22, 2018 (Nov. 22, 2018), vol. 52, pp. 98-109, ISSN 1096-7184 [online].

*Primary Examiner* — Tekchand Saidha
(74) *Attorney, Agent, or Firm* — Wood, Phillips, Katz, Clark & Mortimer

(57) ABSTRACT

Embodiments provide a modified microbe capable of growing in or fermenting a solution, or lignocellulosic hydrolysate, comprising ferulic acid and/or coniferyl aldehyde. The microbe has one or more modifications to provide: (a) a decrease in copy number or expression of a BNA7 gene; (b) an increase in copy number or expression of one or more pentose phosphate pathway genes; and/or (c) localization of one or more products of the pentose phosphate pathway genes to the mitochondria or endoplasmic reticulum. Also provided is a microbe having modified expression or copy number of BNA7 and/or one or more of the pentose phosphate pathway genes. The pentose phosphate pathway genes may in certain embodiments be selected from at least one of ZWF1, TKL1, RPE1 and GND1. Also provided is a method for fermenting a substrate comprising ferulic acid and/or coniferyl aldehyde to produce a fermentation product.

23 Claims, 21 Drawing Sheets

MICROBE HAVING INCREASED TOLERANCE TO PHENOLIC FERMENTATION INHIBITORS

RELATED APPLICATIONS

This application claims priority to U.S. provisional application Ser. No. 62/746,178 filed Oct. 16, 2018, which is incorporated by reference in its entirety.

TECHNICAL FIELD

Embodiments disclosed herein provide a modified microbial strain capable of growing or fermenting a substrate solution comprising one or more phenolic inhibitors. Further provided is a method to use such strain.

BACKGROUND

Though food crops high in starch are commonly used for biofuel production, their use as a feedstock is not ideal given multiple issues including food security and high cost. Therefore, the emerging biofuels industry has turned towards lignocellulosic biomass as a feedstock such as, but not limited to, those found in agricultural and forestry residues, as well as energy crops including grasses grown on marginal lands.

The bioconversion of lignocellulose to fuels often involves the hydrolysis of the lignocellulosic biomass into simple sugars, which are subsequently converted to biofuels and other chemicals by fermentation using yeast. However, in addition to the release of sugars, the hydrolysis also generates a complex mix of biologically toxic compounds derived from lignin, including furan derivatives, organic acids and phenolic compounds.

Among these inhibitory products, phenolic compounds are generally regarded as the most toxic as they are typically capable of severely inhibiting yeast growth and fermentation at minute quantities. For example, ferulic acid, 4-hydroxybenzoic acid and coniferyl aldehyde kill the commercial *Saccharomyces cerevisiae* ethanol red when present at 5 mM, 11 mM and 1 mM respectively (Adeboye et al., 2014, AMB Express, 4, 46-46). The concentrations of these inhibitors in sugar hydrolyzates can vary, but are often found at concentrations that can negatively impact the growth or fermentation of the yeast. Sodium hydroxide hydrolysis of rice straw yields 0.985 mM ferulic acid (Hou, J. et al., 2017, Journal of Cleaner Production, 165, 1107-1114), whereas acid treated corn stover yields 2 mM ferulic acid (Lopez et al., 2004, Applied Microbiology and Biotechnology, 64, 125-131). While 4-hydroxybenzoic acid is present at 0.0002 mM in acid hydrolyzed corn stover (Du et al., 2010, Biotechnology and Bioengineering, 107, 430-440), its concentration reaches 0.036 mM in acid hydrolyzed spruce (Larsson et al., 1999, Applied Biochemistry and Biotechnology, 77, 91-103).

Given the fact that the concentrations of these phenolics found in typical hydrolysates are often toxic, mitigation strategies are required for efficient microbial-based fermentation to occur. To limit the effect of phenolic inhibitors on microbial growth and fermentation, different strategies are under development. One approach is to remove the compounds from the hydrolysate as they form. However, this remains a very expensive and time consuming approach.

The following disclosure seeks to address this and/or to provide useful alternatives to known approaches to reduce the impact of these molecules on microbial growth and fermentation.

SUMMARY

The present disclosure is based on the identification of genes for targeted improvements in the tolerance of a microbial or yeast cell to ferulic acid and/or coniferyl aldehyde, both of which are potent phenolic inhibitors that are often found at inhibitory concentrations in lignocellulosic hydrolysates.

In particular, according to one aspect, the disclosure is based on the finding that the tolerance of a yeast cell to ferulic acid (also referred to herein as "FA") was improved by the deletion of BNA7, which is a gene involved in the tryptophan catabolic pathway and that encodes a formylkynurenine formamidase enzyme. In addition, it has been found that the deletion of one or more of ZWF1, TKL1, RPE1 and GND1 involved in the pentose phosphate pathway reduces the tolerance of the yeast to coniferyl aldehyde, thereby implicating these genes in conferring improved tolerance to this inhibitor. The gene ZWF1 encodes glucose-6-phosphate dehydrogenase, an enzyme which catalyses the rate-limiting step of the pathway and that generates NADPH. TKL1 encodes a transketolase and RPE1 encodes D-ribulose-5-phosphate 3-epimerase. GND1 encodes a 6-phosphogluconate dehydrogenase and is the third enzyme of the oxidative branch of the pentose phosphate pathway and that also generates NADPH.

Moreover, according to another aspect, the disclosure is based on the finding that the ZWF1 gene product partially localizes to the mitochondria and endoplasmic reticulum upon exposure to coniferyl aldehyde (also referred to herein as "CA"). As demonstrated herein, it is believed that reactive oxygen species (also referred to herein as "ROS") are generated during exposure of the yeast to coniferyl aldehyde and such species become concentrated at and around the endoplasmic reticulum and mitochondria. It has also been shown by the inventors that Zwf1 becomes enriched at these organelles upon exposure of the yeast to coniferyl aldehyde. Without being bound by theory, it is believed that, upon exposure to coniferyl aldehyde, the enrichment of the ZWF1 gene product to the mitochondria and endoplasmic reticulum induces the pentose phosphate pathway and concentrates the enzymes of this pathway to these specific sites to enhance tolerance to this inhibitor. While not being bound by theory, it is believed that the Zwf1 enzyme increases NADPH at these sites and that its enrichment, in turn, reduces the accumulation of ROS at these sites. Similar findings were established with other proteins of the pentose phosphate pathway. Accordingly, the disclosure also provides a yeast strain having one or more genetic modifications to provide an increase in the localization of genes encoding proteins in the pentose phosphate pathway to the mitochondria or endoplasmic reticulum. Such modification may include a tag that targets the gene product to these organelles within the cell. Localization tags (also referred to as signal sequences) are known to those of skill in the art and include DNA sequences that encode short amino acid sequences operatively linked to a DNA sequence encoding a protein of the pentose phosphate pathway, and that have the ability to target the protein to these organelles. Thus, according to one embodiment, there is provided a modified yeast strain capable of growing or fermenting a substrate in a solution or lignocellulosic hydrolysate comprising ferulic acid and/or coniferyl aldehyde. The yeast strain has one or more modifications to provide: (a) a decrease in copy number or expression of a BNA7 gene; (b) an increase in copy number or expression of one or more pentose phosphate pathway genes; and/or (c) localization of one or more products of the pentose phosphate pathway genes to the mitochondria or endoplasmic reticulum.

The pentose phosphate pathway genes may in certain embodiments be selected from at least one of ZWF1, TKL1, RPE1 and GND1.

In certain embodiments, the yeast strain comprises: (a) a decrease in copy number or expression of the BNA7 gene; and (b) an increase in copy number of the one or more genes involved in the pentose phosphate pathway. In further embodiments, the yeast strain comprises: (a) a decrease in copy number or expression of a BNA7 gene; and (b) an increase in copy number of the ZWF1 gene.

In further embodiments, the yeast strain comprises: (a) a decrease in copy number or expression of a BNA7 gene; and (b) localization of one or more products of the pentose phosphate pathway genes to the mitochondria or endoplasmic reticulum.

In yet further embodiments, the yeast strain comprises: (a) a decrease in copy number or expression of the BNA7 gene; and (b) localization of the gene product of ZWF1 to the mitochondria or endoplasmic reticulum.

In a further example, the decrease in expression of the BNA7 gene is caused by a deletion or inactivation of the BNA7 gene, or a modification of a regulatory element that controls expression of the BNA7 gene in the genome of the yeast.

In another embodiment, the increase in expression of the one or more genes selected from ZWF1, TKL1, RPE1 or GND1 is caused by an increase in copy number of the one more genes, or a modification of a regulatory element that controls expression of the one or more genes in the genome of the yeast.

In another embodiment, the yeast strain is from the genus of *Saccharomyces, Candida, Pichia,* or *Kluyveromyces*. In another embodiment, the yeast strain is a *Saccharomyces cerevisiae* strain.

Yet further, the yeast strain may comprise a nucleotide sequence operatively linked to one or more of the genes of the pentose phosphate pathway, which sequence encodes for an amino acid tag that localizes the one or more products of the genes to the mitochondria or endoplasmic reticulum of the cell.

The nucleotide sequence in certain embodiments is operatively linked to the ZWF1 gene so that when the ZWF1 gene is expressed, a resultant gene product, Zwf1, comprises the amino acid tag operatively linked thereto, thereby localizing the Zwf1 gene product to the mitochondria or endoplasmic reticulum of the cell.

In further non-limiting embodiments, the strain comprises a genetic modification to increase a copy number of the ZWF1 gene.

While modified yeast strains were shown to exhibit tolerance to one or more phenolic inhibitors, it should be understood that other microbes could be genetically altered to possess such tolerance as well. This includes bacteria and fungi, including filamentous fungi. While bacteria do not possess organelles, according to select embodiments, they could be modified to provide a decrease in copy number or expression of the BNA7 gene and/or an increase in copy number or expression of one or more pentose phosphate pathway genes so as to exhibit such tolerance. Bacteria contain genes encoding for formylkynurenine formamidase and glucose-6-phosphate dehydrogenase, among other genes that can be modified as set forth herein to confer resistance to phenolic inhibitors.

Thus, according to a further embodiment, there is provided a modified microbe having a decrease in copy number or expression of a BNA7 gene; and/or an increase in copy number or expression of one or more pentose phosphate pathway genes relative to a parental or wild-type strain. Such microbe can be a yeast, a bacterium or a fungi.

Further provided is a method for fermenting a substrate solution or a lignocellulosic hydrolysate comprising ferulic acid and/or coniferyl aldehyde to produce a fermentation product. The method comprises exposing the solution or the lignocellulosic hydrolysate to a microbe or yeast strain as described herein to produce the fermentation product. The fermentation product includes an alcohol, such as ethanol, butanol or 2,3-butanediol or other fermentation products such as lactic acid, acetic acid, citric acid, ascorbic acid, butyric acid, proprionic acid, fumaric acid, malic acid, succinic acid, propanediol, butanediol, butadiene, xylitol, sorbitol, mannitol, erythritol, acetone, vanillin, caffeic acid, cinnamic acid and p-hydroxycinnamic acid.

Figure 1:
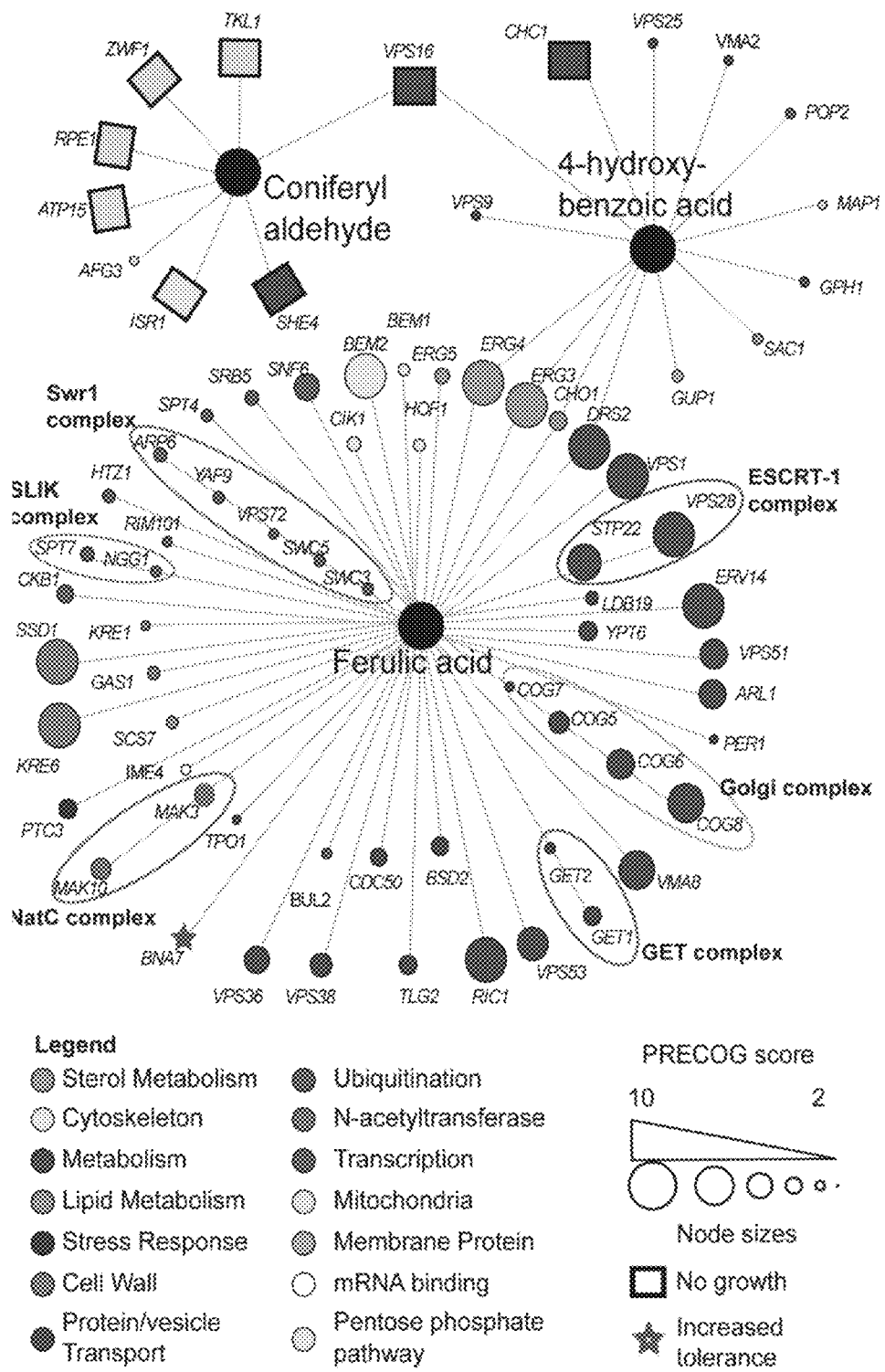
FIG. 1 is a diagram showing the chemogenomic network of coniferyl aldehyde, ferulic acid and 4-hydroxybenzoic acid (shown as black nodes) in the center of each depiction. Deletion mutants identified in the screen are represented by nodes corresponding to the biological processes indicated in the legend. The size of each node corresponds to the sensitivity to the different compounds based on a Presentation and Characterization of Growth-data (PRECOG) analytics software score with no growth or lethal hits indicated by a square node and suppressor or improved growth indicated by a star.

The details of one or more exemplary embodiments are set forth in the accompanying drawings and the description below. Other features, objects and advantages of the disclosure will be apparent from the description and drawings and from the claims.

DETAILED DESCRIPTION

Substrate

As discussed, the modified microbe, such as a yeast strain, exhibits increased tolerance to phenolic inhibitors. In one non-limiting embodiment, the inhibitors are derived from a lignocellulosic feedstock. Thus, in select embodiments, the substrate for fermentation by the modified microbe or yeast strain may be a lignocellulosic hydrolysate comprising sugar as well as one or more phenolic inhibitor. In a further embodiment, the substrate is a solution having one or more inhibitory phenolics derived from any natural or man-made source.

The feedstock includes, but is not limited to, any type of plant biomass such as, but not limited to, non-woody plant biomass, cultivated crops such as, but not limited to grasses, for example, but not limited to, C4 grasses, such as switch grass, cord grass, rye grass, miscanthus, reed canary grass, or a combination thereof, sugar processing residues, for example, but not limited to, bagasse, such as sugar cane bagasse, beet pulp, or a combination thereof, agricultural residues, for example, but not limited to, soybean stover, corn stover, rice straw, rice hulls, barley straw, sugar cane straw, corn cobs, wheat straw, canola straw, oat straw, oat hulls, corn fiber, or a combination thereof, forestry biomass for example, but not limited to, recycled wood pulp fiber, sawdust, hardwood, for example aspen wood, softwood, or a combination thereof. Furthermore, the lignocellulosic feedstock may comprise cellulosic waste material or forestry waste materials such as, but not limited to, newsprint, cardboard and the like. Lignocellulosic feedstock may comprise one species of fiber or, alternatively, lignocellulosic feedstock may comprise a mixture of fibers that originate from different lignocellulosic feedstocks.

To produce the substrate, the lignocellulosic feedstock may be subjected to one or more of chemical, heat, mechanical and biological treatments to yield a lignocellulosic hydrolysate comprising sugar and the one or more phenolic inhibitors. To produce the lignocellulosic hydrolysate, a pretreatment method may be employed. Such methods disrupt the fiber structure and increase the surface area of the lignocellulosic feedstock to make the cellulose component accessible to subsequent hydrolysis, such as by hydrolytic enzymes including cellulases. In one embodiment, the pretreatment is carried out by chemical action. For example, the pretreatment may include the use of acid or alkali. The pretreatment may also employ heat or solvents as would be appreciated by those of skill in the art.

Phenolic inhibitors are released during pretreatment or other treatment of the feedstock typically employing chemical and/or heat treatment. Such inhibitors are often carried through into fermentation and reduce the efficiency of sugar fermentation by the yeast or reduce growth of the yeast strain relative to their absence. Similar inhibition has been found with bacterial and fungal fermentations. Phenolic inhibitors often arise from the lignin contained within the feedstock. Lignin functions as a structural component of plants that contains aromatic components and its partial degradation results in the release of compounds containing aromatics. As noted, three inhibitors present in lignocellulosic hydrolysates include: ferulic acid (4-hydroxy-3-methoxycinnamic acid), 4-hydroxybenzoic acid and coniferyl aldehyde (4-hydroxy-3-methoxycinnamaldehyde). Other inhibitors may be present as well, including acetic acid, furfural, vanillin, p-coumaric acid and hydroxymethylfurfural (HMF).

The lignocellulosic hydrolysate may arise from a variety of stages in the process. As noted, after pretreatment, the cellulose is hydrolyzed by cellulase enzymes to release glucose. The pretreated feedstock may be treated with liquid, typically an aqueous solution or process water, to remove components in solution that were released during the prior pretreatment. This includes xylose, among other C5 sugars, along with the inhibitors released during pretreatment. A liquid stream resulting from such treatment comprises these components. This stream may be fermented by a microbe, such as a yeast capable of fermenting xylose and/or other C5 and C6 sugars. In another embodiment, the pretreated feedstock comprising cellulose is fed to a cellulose hydrolysis that employs cellulase enzymes to produce a lignocellulosic hydrolysate comprising glucose, as well as the sugars released from xylan during pretreatment. Often such a stream is referred to as a mixed sugar stream. The mixed sugar stream comprising inhibitors generated during pretreatment, glucose derived from cellulose and sugars derived from xylan, may be fermented by the yeast strain to yield a fermentation product. A person of ordinary skill in the art can envisage other streams arising from lignocellulosic conversion processes that can be fermented by the microbe or yeast strain described herein to produce the fermentation product.

Microbe

The microbe used to produce the fermentation product may be a yeast, bacterium or fungus. In one advantageous embodiment, the microbe is a yeast cell.

A variety of modified yeast strains can be used in select embodiments. The yeast strain may be from a genus selected from *Saccharomyces, Candida, Pichia, Pachysolen, Rhodotorula, Hansenula, Debaryomyces, Kluyveromyces* and i *Schizosaccharomyces*.

Non-limiting examples of yeast strains for use in select embodiments include *Saccharomyces cerevisiae, Candida tropicalis, Candida guilliermondii, Candida utilis, Candida*

*arabinofermentans, Candida diddensii, Candida Sonorensis, Candida Shehatae, Candida boidinii, Candida paripsilosis, Pichia stipitis, Pichia pastoris, Pachysolen tannophilus, Rhodotorula mucilagiinosa* (formerly *Rhodotorul arubra*), *Hansenula anomala, Hansenula polymorpha, Debaryomyces hansenii, Kluyveromyces marxianus, Kluyveromyces fragilis* and *Schizosaccharomyces pombe*.

The modified yeast strain may be derived from a parental yeast strain that is naturally capable of glucose fermentation, e.g., a species of Saccharomyces. In some embodiments, the modified yeast strain is capable of fermenting xylose present in lignocellulose hydrolysates, such as e.g., a species of *Candida, Pichia,* or *Kluyveromyces,* or a strain that has been modified for enhanced xylose utilization through recombinant or non-recombinant methods. An example of such a strain is described in U.S. Pat. No. 7,527,927. The parental strain may also be prepared by adaptive evolution or random mutagenesis and selection. However, it should be appreciated that the practice of embodiments described herein is not limited by the method used to produce the parental and modified yeast strains.

Additionally or alternatively, the yeast strain may be capable of converting other molecules derived from a lignocellulosic feedstock besides sugar to a desired fermentation product. For example, ferulic acid could be fermented to vanillin using a yeast strain having one or more modification disclosed herein. Other non-sugar components derived from lignocellulosic material could be fermented to a desired fermentation product as well.

A variety of modified bacteria may be used in certain embodiments as well to produce the fermentation product. Examples of bacteria that could be used in the practice of certain embodiments include *Actinomycetes, Rhodococcus, Corynebacterium, Halomonas, Bacillus, Pseudomonas, Escherichia, Lactobacillus, Streptomyces, Amycolatopsis* and *Zymomonas*. Without being limiting, species of bacteria within each mentioned genus have been shown to ferment ferulic acid to vanillin (but at low concentrations due to the inhibitory effect of vanillin). Thus, in certain embodiments, deletion of one or more copies of the BNA7 gene or a reduction in its expression may reduce or eliminate such inhibitory effect.

Fungi, including filamentous fungi, may also be used in certain embodiments to produce a desired fermentation product. Examples of fungi include *Schizophyllum, Pycnoporus, Aspergillus* and *Trichoderma*.

In select embodiments, the modified microbe or yeast strain disclosed herein exhibits a specific rate of glucose or xylose fermentation to a fermentation product that is increased by at least 1.3-fold (e.g., 1.5-fold, 2-fold, or greater), relative to a corresponding parental or wild-type yeast in a solution or lignocellulosic hydrolysate comprising coniferyl aldehyde, ferulic acid, or both inhibitors, measured under otherwise identical fermentation conditions.

In other embodiments, the modified microbe or yeast strain disclosed herein exhibits a specific rate of conversion of a substrate to a fermentation product that is less than or comparable to a parental or wild-type yeast, but exhibits other desirable characteristics for industrial applications, such as increased growth as measured by biomass production in the presence of one or more inhibitors. For example, a modified microbe or yeast strain disclosed herein may exhibit an increase in growth on a substrate comprising coniferyl aldehyde and/or ferulic acid by at least 1.1 fold (e.g., 1.2-fold, 1.3-fold, 2-fold, or greater), relative to a corresponding parental or wild-type microbe in a solution or lignocellulosic hydrolysate comprising coniferyl aldehyde, ferulic acid, or both inhibitors, measured under otherwise identical growth conditions. Growth of a modified microbe or yeast strain is determined by measuring optical density (OD) at 600 nm for 22 hours and compared to a wild-type or parental strain under identical growth conditions that are optimal for the strain.

Fermentation Product

The term "fermentation product" refers to a fuel and/or chemical derived from any component in a lignocellulosic hydrolysate, such components including but not limited to sugars, sugar breakdown products and/or phenolic compounds. This term also includes intermediates or precursors that can be used for producing such fuel or chemical.

Examples of fuels include ethanol, butanol and 2, 3-butanediol.

The chemical may be for use in polymer, food and pharmaceutical applications, among others. Examples of such chemicals include 1,3 butadiene and 1,3-propanediol; sugar alcohols such as sorbitol, xylitol, mannitol, erythritol; organic acids such as lactic acid, citric acid, butyric acid, proprionic acid, fumaric acid, malic acid and succinic acid; and aromatics or ring compounds such as caffeic acid, vanillin, cinnamic acid and p-hydroxycinnamic acid.

As discussed, ferulic acid is a phenolic inhibitor present in lignocellulosic hydrolysates that can be converted to the chemical vanillin by a microbe having the genetic modifications disclosed herein. In another embodiment, p-coumaric acid derived from the hydrolysis of lignocellulosic feedstock can be converted to caffeic acid by such microbes. Caffeic acid has been reported to possess antioxidant, antitumor, antiviral and anti-inflammatory activities (Hernàndez-Chàvez et al., 2019, Electronic Journal of Biotechnology, 38, 19-26). Likewise, cinnamic acid and p-hydroxycinnamic acid can be produced from components found in lignocellulosic hydrolysates.

Decrease in Expression or Copy Number of BNA7

As discussed, the microbe of yeast strain may have a decrease in the copy number or expression of BNA7, which is the gene involved in the tryptophan catabolic pathway and encodes a formyl-kynurenine formamidase enzyme. Decreasing the copy number or expression of BNA7 in yeast confers improved resistance to ferulic acid relative to a wild-type or parental strain. However, this enzyme is also present in prokaryotic cells and thus decreasing its copy number or expression in bacterial cells is encompassed by certain embodiments.

As used herein, a "decrease in expression" means that the modified microbe or yeast exhibits reduced expression of the gene relative to (i) a wild-type strain, and/or (ii) a parental strain from which the modified microbe or yeast is derived. Expression of the gene from the two strains being compared is measured under identical culture conditions (time, temperature, pH, etc).

It will be appreciated that a decrease in expression relative to the reference strain includes elimination or reduction of the expression of the BNA7 gene. For the purposes described herein, the decrease in expression means at least about a 1.2-fold decrease in the expression of the gene in the modified microbe or yeast as compared to the expression level of the BNA7 gene in the parental or wild-type microbe or yeast when grown under identical conditions of medium composition, temperature, pH, cell density and age of culture. For example, the level of expression of BNA7 in the microbe or modified yeast strain may be decreased by 1.2-, 1.5, 1.7, 2-, 2.5-, 3-, 5, 10-, 20-, 50-fold or more relative to the expression of that same gene in the parental or wild-type microbe or yeast strain when grown or cultured under identical culture conditions.

A decrease in expression of the BNA7 gene is determined by western blot analysis as described herein or RT-qPCR, which is a technique that is known in the art. Protein quantification by western blot analysis is described in more detail in Example 7.

For the purposes described herein, the term "decreased copy number" means that at least one less copy of at least the coding region of a given gene is present in the modified microbe or yeast as compared to the copy number of the same gene or genes present in the parental and/or wild-type strain. A decrease in copy number of the BNA7 gene can be measured by comparing the copy numbers of the BNA7 gene in the modified microbe or yeast to a wild-type or a parental strain by PCR or any other suitable technique known in the art.

Various recombinant techniques could be utilized to decrease the expression or copy number of BNA7. A non-limiting example of a technique for reducing the copy number of BNA7 is set forth below. Techniques for reducing the expression of the gene are well known in the art and include, without limitation, transcriptional, post-transcriptional, and translational down-regulation. For example, expression of these genes can be downregulated by antisense oligonucleotides, RNA interference, ribozymes, triplex-forming oligonucleotides, and the like.

An example of a method to reduce the copy number of a gene involves creating a knock out strain or a partial knock out strain by homologous recombination. According to one embodiment, only one of a number of gene copies (alleles) is knocked out in the modified microbe or yeast strain. In another embodiment, more than one or all gene copies of the BNA7 gene are knocked out. This method may involve creating a DNA construct containing a replacement sequence. Such replacement sequence can include any suitable sequence known to those of ordinary skill in the art. In one embodiment, a drug resistance marker may replace the BNA7 gene. The construct will also contain a sequence having homology to the BNA7 sequence. The construct can be delivered to the microbial or yeast cells by any known transformation method. A typically employed method for yeast is transformation with polyethyleneglycol (PEG), which is also well known to those of skill in the art, although other techniques can be utilized, such as electroporation. Once the DNA is introduced into the cell, the method typically relies on the repair mechanisms of the yeast cell to recombine the DNA construct into the genome. This results in the sequence of the gene being altered. In one non-limiting embodiment, the gene will be translated into a non-functional protein or, in other embodiments, translation is prevented. Often, a drug selection marker on the construct is used to select for cells in which the recombination event has occurred.

It will be appreciated that any number of nucleotides can be knocked out, from a single base to the entire BNA7 gene. In some embodiments, complete or near-complete deletion of the gene sequence is contemplated. For example, the knock-out may include elimination of at least 5% to 100% of the BNA7 gene.

In addition, a CRISPR/Cas9 system can be used to reduce the copy number or expression of a gene. By delivering the Cas9 nuclease complexed with a synthetic guide RNA (gRNA) into a cell, the genome of the microbial or yeast cell can be cut at a desired location, allowing existing genes to be removed. Other nuclease-based gene editing systems, such as zinc finger nucleases and TALENs can be utilized as well to reduce the copy number or expression of the BNA7 gene.

In another non-limiting embodiment, the BNA7 gene can be modified to disrupt a transcription or translation initiation sequence or to introduce a frameshift mutation in the transcript encoding the polypeptide. Other methods of reducing the gene expression include post-transcriptional RNA silencing methodologies. Examples of such methodologies include antisense RNA and RNA interference (RNAi). Antisense techniques involve introducing a nucleotide sequence complementary to the transcript of the BNA7 gene such that the complementary antisense nucleotide sequence hybridizes to the target gene transcript. This reduces or eliminates the number of transcripts available to be translated into the BNA7 gene product. Techniques for expressing an antisense RNA are well established in the art. Without being limiting, RNAi methodologies include double stranded RNA (dsRNA), short hairpin RNAs (shRNAs), and small interfering RNAs (siRNAs). Such technologies are known to those of skill in the art.

Other non-limiting methods for decreasing the expression of BNA7 further include disruption or replacement of regulatory sequences, such as a promoter of the gene. The consequence of such disruption or replacement is that the transcription of the BNA7 gene can be reduced or eliminated. For example, the promoter of the gene can be replaced with a weak promoter. For instance, when a weak promoter is operably linked with the coding sequence of an endogenous polypeptide, transcription of BNA7 will be reduced or eliminated.

Increase in Copy Number or Expression of Genes in the Pentose Phosphate Pathway

In certain embodiments, the modified microbe or yeast may have an increase in copy number or expression of one or more genes involved in the pentose phosphate pathway. Such increase in copy number or expression advantageously provides increased tolerance to coniferyl aldehyde found in many lignocellulosic hydrolysates. The genes in the pentose phosphate pathway may be selected from at least one of ZWF1, TKL1, RPE1 and GND1. In one non-limiting embodiment, the modified microbe or yeast has an increase in copy number or expression of at least ZWF1.

As used herein, an "increase in expression" means that the modified microbe or yeast exhibits increased expression of the gene relative to (i) a wild-type strain, and/or (ii) a parental strain from which the modified microbe or yeast is derived. Expression of the gene from the two strains being compared is measured under identical culture conditions (time, temperature, pH, etc).

For the purposes described herein, the increase in expression may include at least about a 1.1-fold increase in the expression of the gene in the modified microbe or yeast as compared to the expression level of the ZWF1 gene in the parental or wild-type microbe or yeast when grown under identical conditions of medium composition, temperature, pH, cell density and age of culture. For example, the level of expression of ZWF1 in the modified microbial or yeast strain may be increased by 1.1-, 1.2-, 1.5, 1.7, 2-, 2.5-, 3-, 5, 10-, 20-, 50-fold or more relative to the expression of that same gene in the parental or wild-type microbe or yeast strain when grown or cultured under identical culture conditions.

An increase in expression of the ZWF1 gene is determined by western blot analysis as described herein or RT-qPCR, which is a technique that is known in the art. Protein quantification by western blot analysis is described in more detail in Example 7.

For the purposes described herein, the term "increased copy number" means at least one additional copy of at least the coding region of a given gene is present in the modified microbe or yeast as compared to the copy number of the same gene or genes present in the parental and/or wild-type microbe or yeast. An increase in copy number of the ZWF1 gene can be measured by comparing the copy numbers of the ZWF1 gene in the modified microbe or yeast to wild-type or a parental strain by rPCR or any other suitable technique known in the art.

The extra copies of a given gene in the pentose phosphate pathway may be integrated into the genome of the modified microbe or yeast strain or may be present on one or more autonomously replicating vectors or plasmids present in the modified microbe or yeast strain.

Without being limiting, in one embodiment, the copy number of a given gene can be increased by insertion of the gene into the genome of the microbe or yeast by a knock-in technique. A gene knock-in may involve inserting a gene into a specific locus within the microbe or yeast genome. In certain embodiments, gene knock-in technology may alter the genetic locus of interest via a one-for-one substitution of a given DNA sequence or by the addition of a sequence that is not otherwise found in the microbial or yeast genome. Non-limiting examples of methods for increasing the copy number of a gene in the pentose phosphate pathway includes homologous recombination as described above. In addition, the CRISPR/Cas9 system can be used to increase the copy number or expression of a gene. By delivering the Cas9 nuclease complexed with a synthetic guide RNA (gRNA) into the microbe or yeast cell, the genome can be cut at a desired location, allowing the addition of new genes or sequences thereof. Other nuclease-based gene editing systems, such as zinc finger nucleases and TALENs can be utilized as well to increase the copy number or expression of a pentose phosphate pathway gene.

Techniques for producing overexpression of one or more of the foregoing genes are well known in the art and include, without limitation, transcriptional, post-transcriptional, and translational upregulation.

For example, transcriptional upregulation may involve introducing regulatory sequences, such as a promoter sequence, into the microbial or yeast genome that increase transcription of a gene. For instance, when a strong promoter is operably linked with the coding sequence of an endogenous polypeptide, transcription of the gene will be increased. Any of the foregoing genetic modification techniques could be employed to introduce a promoter or suitable strength upstream of a gene of interest.

Without being limiting, it will be appreciated that increased expression of genes of the pentose phosphate pathway could potentially lead to cell death. Consequently, the expression levels of one or more genes in the pentose phosphate pathway could be adjusted using known techniques to ensure that overexpression does not result in death of the modified microbe or yeast cell. For example, a promoter that drives expression of a pentose phosphate gene could be selected that is of a suitable strength to provide a desired level of expression that does not lead to cell death or an inducible promoter could be introduced so expression of the gene occurs only under certain conditions. The selection of a suitable expression system for introduction into the microbe or yeast cell to prevent cell death is within the skill of a person of skill in the art.

Increasing the Localization of Gene Products of the Pentose Phosphate Pathway to the Mitochondria or Endoplasmic Reticulum As discussed, the disclosure also provides a yeast or fungal strain having one or more genetic modifications to provide an increase in localization of genes encoding proteins in the pentose phosphate pathway to the mitochondria and/or endoplasmic reticulum. The localization of the proteins to these sites may reduce ROS, which have been shown in the present disclosure to accumulate at the mitochondria and endoplasmic reticulum upon exposure of the yeast or fungal cell to coniferyl aldehyde. Such modification may include a tag that targets the gene product to these organelles within the cell. Localization tags are known to those of skill in the art and include DNA sequences that encode short amino acid sequence operatively linked to a protein of the pentose phosphate pathway, and that have the ability to target the protein to these organelles.

Without being limiting, the mitochondrial tag may be a polypeptide or peptide that directs a newly synthesized protein to the mitochondria. In certain non-limiting embodiments, the tag may comprise an alternating pattern of hydrophobic and positively charged amino acids to form an amphipathic helix, although other structures may be employed. In further embodiments, the mitochondrial targeting signals are cleaved once targeting is complete. Without being limiting, the mitochondrial tag may comprise a mitochondrial targeting sequence (MTS). For example, the MTS may be a sequence derived from the ALD5 protein, which is confirmed to localize to the mitochondria, and has a sequence of MLSRTRAAAPNSRIFTRSLLRLY (SEQ ID NO:1).

Likewise, without being limiting, the endoplasmic reticulum tag may be a short peptide sequence that directs a protein of the pentose phosphate pathway to the endoplasmic reticulum. For translocation to the endoplasmic reticulum in yeasts, a short tag comprising a 4-amino-acid retention sequence HDEL for transport to the lumen of the ER may be located at the C-terminal end of the protein.

Although the above discussion describes the use of molecular biology techniques to produce the modified microbe or yeast strain, the strain may also be produced at least partially by random mutagenesis and selection techniques. For example, a parental microbial or yeast strain may be subjected to irradiation or chemical mutagenesis to create a library of mutated strains, which are then screened for a desired altered phenotype.

EXAMPLES

Strains and Plasmids

A variety of yeast strains were utilized in the examples. Yeast strains were derivatives of the haploid BY4741 strain and are listed in Table 1 below. All strains described herein were PCR confirmed.

TABLE 1

Strains used in experiments

| Strain | Auxotrophies |
| --- | --- |
| BY4741 | MATa his3Δ1 leu2Δ0 met15Δ0 ura3Δ0 |
| YKB4212 | MATa his3Δ1 leu2Δ0 met15Δ0 ura3Δ0 SEC13-RFP::kanMX |
| YKB4825 | MATa his3Δ1 leu2Δ0 met15Δ0 ura3Δ0 ZWF1-GFP::HIS |
| YKB4649 | MATa his3Δ1 leu2Δ0 met15Δ0 ura3Δ0 bna7Δ::kanMX |
| YKB4799 | MATa his3Δ1 leu2Δ0 met15Δ0 ura3Δ0 aro8Δ::kanMX |
| YKB4798 | MATa his3Δ1 leu2Δ0 met15Δ0 ura3Δ0 bna2Δ::kanMX |

TABLE 1-continued

Strains used in experiments

| Strain | Auxotrophies |
| --- | --- |
| YKB4844 | MATa his3Δ1 leu2 Δ 0 met15Δ0 ura3Δ0 bna6Δ::kanMX |
| YKB4845 | MATa his3Δ1 leu2Δ0 met15Δ0 ura3Δ0 bna5Δ::kanMX |
| YKB4846 | MATa his3Δ1 leu2Δ0 met15Δ0 ura3Δ0 bna4Δ::kanMX |
| YKB4729 | MATa his3Δ1 leu2Δ0 met15Δ0 ura3Δ0 bna1Δ::kanMX |
| YKB4794 | MATa his3Δ1 leu2Δ0 met15Δ0 ura3Δ0 zwf1Δ::kanMX |
| YKB4796 | MATa his3Δ1 leu2Δ0 met15Δ0 ura3Δ0 tkl1Δ::kanMX |
| YKB4795 | MATa his3Δ1 leu2Δ0 met15Δ0 ura3Δ0 rpe1Δ::kanMX |
| YKB4797 | MATa his3Δ1 leu2Δ0 met15Δ0 ura3Δ0 gnd1Δ::kanMX |
| YKB4850 | MATa his3Δ1 leu2Δ0 met15Δ0 ura3Δ0 gnd2Δ::kanMX |
| YKB4847 | MATa his3Δ1 leu2Δ0 met15Δ0 ura3Δ0 sol2Δ::kanMX |
| YKB4848 | MATa his3Δ1 leu2Δ0 met15Δ0 ura3Δ0 sol3Δ::kanMX |
| YKB4851 | MATa his3Δ1 leu2Δ0 met15Δ0 ura3Δ0 tal1Δ::kanMX |
| YKB2500 | MATa his3Δ1 leu2Δ0 met15Δ0 ura3Δ0 PEX3-RFP::kanMX |
| YKB4838 | MATa his3Δ1 leu2Δ0 met15Δ0 ura3Δ0 zwf1Δ::kanMX CIT1-RFP::kanMX |
| YKB4841 | MATa his3Δ1 leu2Δ0 met15Δ0 ura3Δ0 SOL2-GFP::HIS |
| YKB4842 | MATa his3Δ1 leu2Δ0 met15Δ0 ura3Δ0 SOL3-GFP::HIS |
| YKB4824 | MATa his3Δ1 leu2Δ0 met15Δ0 ura3Δ0 RPE1-GFP::HIS |
| YKB4852 | MATa his3Δ1 leu2Δ0 met15Δ0 ura3Δ0 TAL1-GFP::HIS |
| YKB4823 | MATa his3Δ1 leu2Δ0 met15Δ0 ura3Δ0 TKL1-GFP::HIS |
| YKB4840 | MATa his3Δ1 leu2Δ0 met15Δ0 ura3Δ0 ZWF1-GFP::HIS CIT1-RFP::URA3 |
| YKB4839 | MATa his3Δ1 leu2Δ0 met15Δ0 ura3Δ0 ZWF1-GFP::HIS SEC13-RFP::URA3 |
| YKB2683 | MATa/α URA3-52/URA3-52 HIS3/HIS3 LEU2-3_112/LEU2-3_112 TRP1-289/TRP1-289 MAL2-8C/MAL2-8C SUC2/SUC2 |
| YKB4879 | MATa/α bna7Δ/bna7Δ URA3-52/URA3-52 HIS3/HIS3 LEU2-3_112/LEU2-3_112 TRP1-289/TRP1-289 MAL2-8C/MAL2-8C SUC2/SUC2 |

Statistics

Student t-tests and standard deviations were calculated for three experimental replicates using the GraphPad™ Prism 6.05 software (GraphPad™ Software Inc., La Jolla, Calif.).

Example 1: Identification of Deletion Mutants having Sensitivity to Ferulic Acid, 4-hydroxy-benzoic acid, or coniferyl aldehyde A yeast chemogenomic screen was carried out using a MATa deletion mutant array containing >4,300 yeast mutants. The yeast mutants were pinned onto yeast peptone dextrose (YPD) agar plates buffered to pH 5 containing no phenolics or sub-lethal concentrations of either ferulic acid, 4-hydroxybenzoic acid or coniferyl aldehyde.

In particular, the MATa yeast deletion mutant array collection (~4,200 mutants) was arrayed in duplicate and condensed at a density of 1536 colonies per plate on YPD agar (1% Yeast Extract, 2% Bacto peptone, 2% agar, 0.03% Tryptophan and 2% Glucose) plates supplemented with G418 using a Singer RoToR HDA (Singer Instruments). The condensed arrays were pinned onto YPD agar plates adjusted to pH 5 containing either 6 mM ferulic acid (Sigma; cat. #128708), 1 mM coniferyl aldehyde (Sigma; cat. #382051) or 25 mM 4-hydroxybenzoic acid (Sigma; cat. #240141). To control for any growth defects at pH 5, the array was also pinned onto pH 5 buffered YPD agar plates. All four genome-wide screens were performed in triplicate and the plates were incubated at 30° C. for 48 hr after which images of each plate were taken for growth assessment of each colony using the SGAtools (http://sgatools.ccbr.utoronto.ca/) described by Wagih et al (2013, Nucleic Acids Research, 41, W591-6). An average growth score of less than −0.3 and greater than 0.3 was used as the cut-off to identify mutants that were sensitive and resistant, respectively, to the three phenolic compounds.

The agar-based chemogenomic screen was confirmed by measuring the growth rate of the identified mutants in liquid YPD medium supplemented with the phenolic compounds. Briefly, overnight cultures of the mutant strains were inoculated into fresh YPD medium and strains were incubated at 30° C. until they reached the mid log phase ($OD_{500}$ 0.5-0.6), prior to being diluted to a final $OD_{600}$ of 0.1 in a BioScreen CTM Honeycomb microplate. The growth assays were performed for each mutant in triplicate in YPD alone (control) or YPD medium supplemented with ferulic acid, 4-hydroxybenzoic acid or coniferyl aldehyde. Using a BioScreen CTM plate reader, the cultures were incubated at 30° C. for 72 hours and $OD_{600}$ readings were taken every 15 min to plot growth curves. Data from the BioScreen CTM were analyzed with the PRECOG software (Fernandez-Ricaud et al., 2016, Nucleic acids research. 41, W591-6) to obtain the doubling time of all the strains. A PRECOG score for each of the strains tested was calculated as the ratio of the doubling time in the presence of the phenolic to the doubling time in the absence of these phenolic compounds. Using a cut-off PRECOG score of >2 and <0.4 strains were identified that were sensitive or tolerant, respectively, to the phenolic compounds. The network plot was performed using the statnet package in the R programming software (Hancock et al., statnet: Software Tools for the Representation).

Visualization, Analysis and Simulation of Network Data

The above screening techniques uncovered 76 mutants with a significant decrease (genes required for tolerance to the phenolic) or increase (suppressors) in fitness compared to the wild-type strain upon exposure to the phenolic inhibitors. The results of the screening are shown in in FIG. 1. The figure depicts a chemogenomic network of coniferyl aldehyde, ferulic acid and 4-hydroxybenzoic acid, each indicated by a black central node. Deletion mutants identified in the screen are mapped on the diagram and depicted by nodes that are color coded by respective biological processes identified in the legend of the figure. The size of the nodes correlates with sensitivity to the different compounds based on the PRECOG score (Fernandez-Ricaud et al., 2016, BMC Bioinformatics. 17, 249), with no growth or lethal hits indicated by a square node and suppressor or improved growth indicated by a star.

The ferulic acid screen identified 64 genes that when deleted made the yeast hypersensitive to the compound, meaning that the gene product is required for growth or confers tolerance to the compound. A suppressor gene (BNA7) was identified that when deleted improved the growth on ferulic acid. The screen also identified 14 deletion mutants that were hypersensitive to 4-hydroxybenzoic acid and nine deletion mutants were hyper-sensitive to coniferyl aldehyde treatment.

Example 2: Gene Ontology Analysis to Identify Molecular Processes

The biological processes underlying the chemogenomic profiles were examined by performing a Gene Ontology (GO) enrichment analysis as described in Robinson et al., 2002, BMC Bioinformatics, 3, 35.

The ferulic acid profile was highly enriched with genes involved in protein targeting to vacuoule ($\rho$=4.4E-08), chromatin modification ($\rho$=5.0 E-06), protein transport ($\rho$=1.5E-05) and golgi vesicle-mediated transport (p =4.7E-05). (Data not shown). The ferulic acid chemogenomic screen identified multiple subunits of protein complexes including the Golgi transport complex, NatC, Swr1 and GET (see FIG. 1).

The chemogenomic profile of 4-hydroxybenzoic acid was also enriched for protein targeting to vacuoule ($\rho$=7.7E-05), along with ergosterol biosynthesis pathway ($\rho$=0.001). Four tolerance genes were shared between ferulic acid and 4-hydroxybenzoic acid (see FIG. 1), all of which have a role in lipid homeostasis.

Coniferyl aldehyde had the least number of genes identified in the screen, most of which displayed a significant growth defect or no growth upon exposure to the compound (FIG. 1).

The screen also identified three genes of the pentose phosphate pathway (ZWF1, TKL1 and RPE1), indicating this pathway has the ability to buffer the toxic effects of coniferyl aldehyde. Based on the limited overlap between coniferyl aldehyde and the other two phenolic compounds, it is believed that coniferyl aldehyde has distinct cellular effects on the yeast cell compared to ferulic acid and 4-hydroxybenzoic acid. Taken together, and without being limited by theory, these results suggest that *S. cerevisiae* utilizes different pathways to improve tolerance to the different phenolic compounds despite their structural similarity.

Example 3: Deletion of BNA7 Confers Tolerance to Ferulic Acid

Figure 2A:
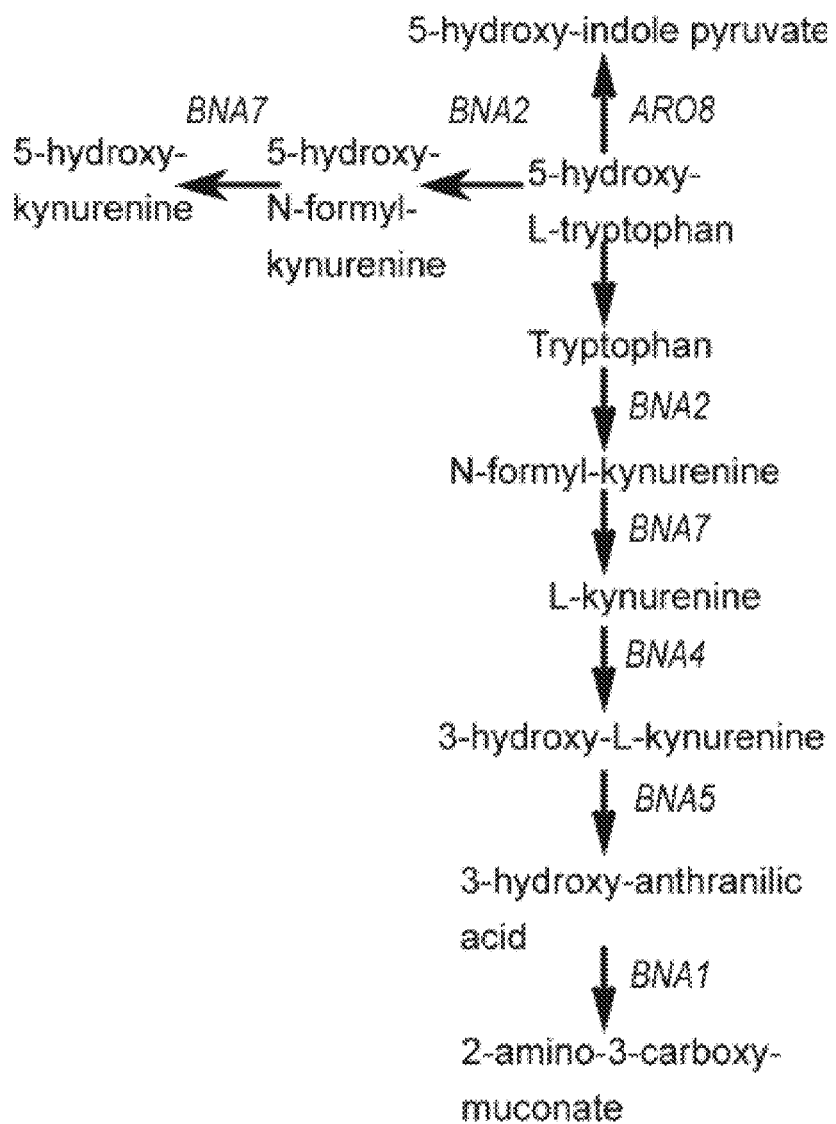
FIG. 2A is a diagram showing the tryptophan catabolic pathway.

As set forth in Example 1, a deletion mutant suppressor (bna7Δ) that conferred resistance or improved growth upon exposure to one of the phenolic compounds was identified in the yeast chemogenomic screen. BNA7 encodes formylkynurenine formamidase, which is an enzyme in the tryptophan catabolic pathway (FIG. 2A).

To confirm that BNA7 is the suppressor gene responsible for resistance to ferulic acid, PCR was conducted to confirm the identity of the mutant.

In addition, deletion mutants were generated for genes involved in the tryptophan catabolic pathway and their growth was assayed on solid media containing 10 mM ferulic acid. In particular, wild type yeast (BY4741) along with deletion mutants aro8Δ (YKB4799), bna7Δ (YKB4649), bna2Δ (YKB4798), bna6Δ (YKB4844), bna5Δ (YKB4845), bna4Δ (YKB4846) and bna1Δ (YKB4729) were grown to mid log phase ($OD_{500}$ 0.5-0.6) in YPD medium prior to being diluted to an $OD_{600}$ of 0.1. Four 10-fold serial dilutions were spotted onto YPD agar plates either containing 10 mM ferulic acid or no ferulic acid. Plates were incubated for 48 hr at 30° C. Images of the plates were taken with the ChemiDoc XRS Molecular Imaging system (Biorad) and images are representative of three biological replicates.

Figure 2B:
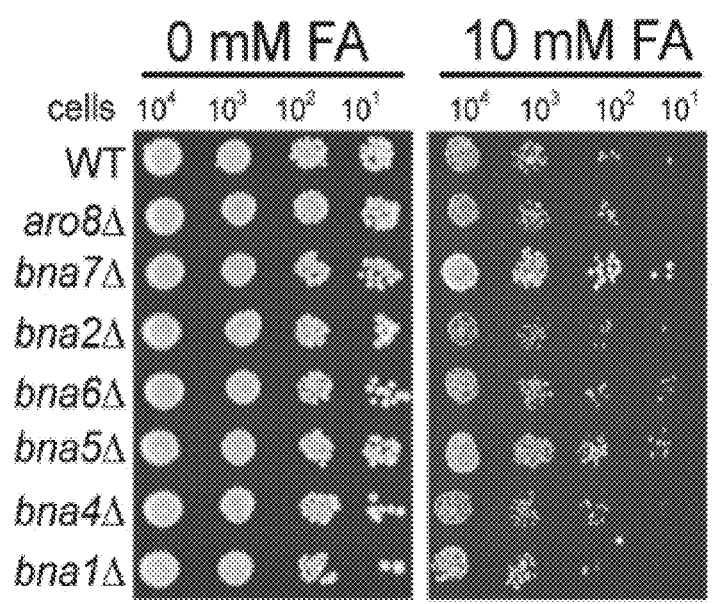
FIG. 2B shows four 10-fold serial dilutions of yeast cultures spotted onto YPD agar plates containing 0 mM ferulic acid or 10 mM of ferulic acid as indicated. The yeast cultures spotted on the agar plates include wild-type (BY4741) as well as the following strains containing deletions of genes encoding for proteins in the tryptophan catabolic pathway: aro8Δ (YKB4799), bna7Δ (YKB4649), bna2Δ (YKB4798), bna6Δ (YKB4844), bna5Δ (YKB4845), bna4Δ (YKB4846) and bna1Δ(YKB4729).

The results are shown in FIG. 2B. As can be seen, deletion of other genes in the pathway (mutants aro8Δ, bna2Δ, bna6Δ, bna5Δ, bna4Δ and bna1Δ) had no effect on ferulic acid tolerance on plates at the concentrations examined.

To further confirm that deletion of BNA7 improves tolerance to ferulic acid in liquid cultures, automated growth curve analysis was performed in triplicate with wild type (BY4741) and bna7Δ (YKB4649) cells in YPD liquid medium without (0 mM FA) or with ferulic acid (10 mM FA). The growth curve analysis was carried out using microplates as per the procedure described in Example 1. The microplates were incubated with shaking at 30° C. for 72 hr and cell density ($OD_{500}$) was measured every 15 minutes using a BioScreen C plate reader.

Figure 2C:
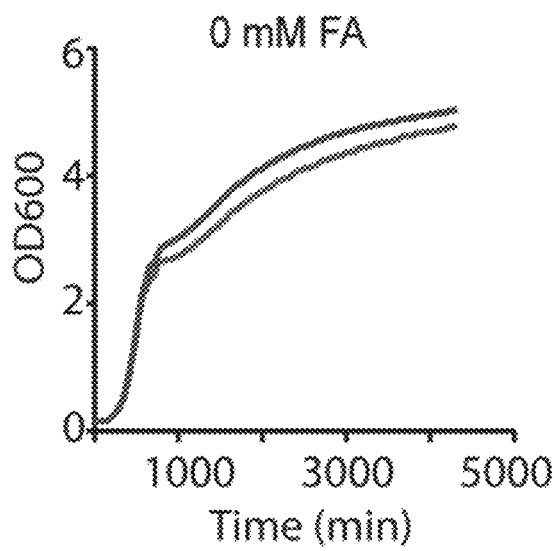
FIG. 2C is a graph showing growth curves of the deletion strain bna7Δ (YKB4649) as measured at $OD_{600}$ in YPD medium without ferulic acid (0 mM FA). The top curve is wild-type (BY4741) and the bottom curve is the deletion strain bna7Δ (YKB4649).
Figure 2D:
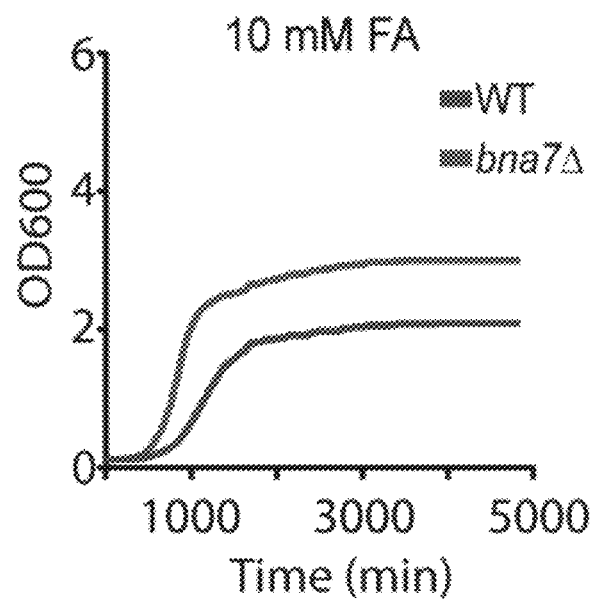
FIG. 2D is a graph showing growth curves of the deletion strain bna7Δ (YKB4649) as measured at $OD_{600}$ in YPD medium with ferulic acid (10 mM FA). The top curve is the deletion strain bna7Δ (YKB4649) and the bottom curve is wild-type (BY4741).

The results are shown in FIG. 2C and FIG. 2D. In FIG. 2C, the top curve is a wild-type strain and the bottom curve is a bna7Δ deletion strain. In the absence of ferulic acid, the growth curves are similar (FIG. 2C). In FIG. 2D, the top curve is a bna7Δ deletion strain. In the presence of 10 mM ferulic acid, the bna7Δ deletion strain exhibits increased growth relative to the wild-type strain.

To confirm that the resistance of bna7Δ was not due to acid tolerance, the impact of the deletion of BNA7 and other genes in the tryptophan catabolic pathway on yeast growth was examined at a lower pH (pH 5). In this experiment, wild-type (BY4741) along with aro8Δ (YKB4799), bna7Δ (YKB4649), bna2Δ (YKB4798), bna6Δ (YKB4844), bna5Δ (YKB4845), bna1Δ (YKB4846) and bna1Δ (YKB4729) were grown to mid-log phase in YPD medium prior to being diluted to an $OD_{500}$ of 0.1. Four 10-fold serial dilutions were spotted onto YPD agar plates adjusted to pH 5 and pH 6.8 (control). Plates were incubated for 48 hr at 30° C. and images are representative of three biological replicates.

Figure 3:
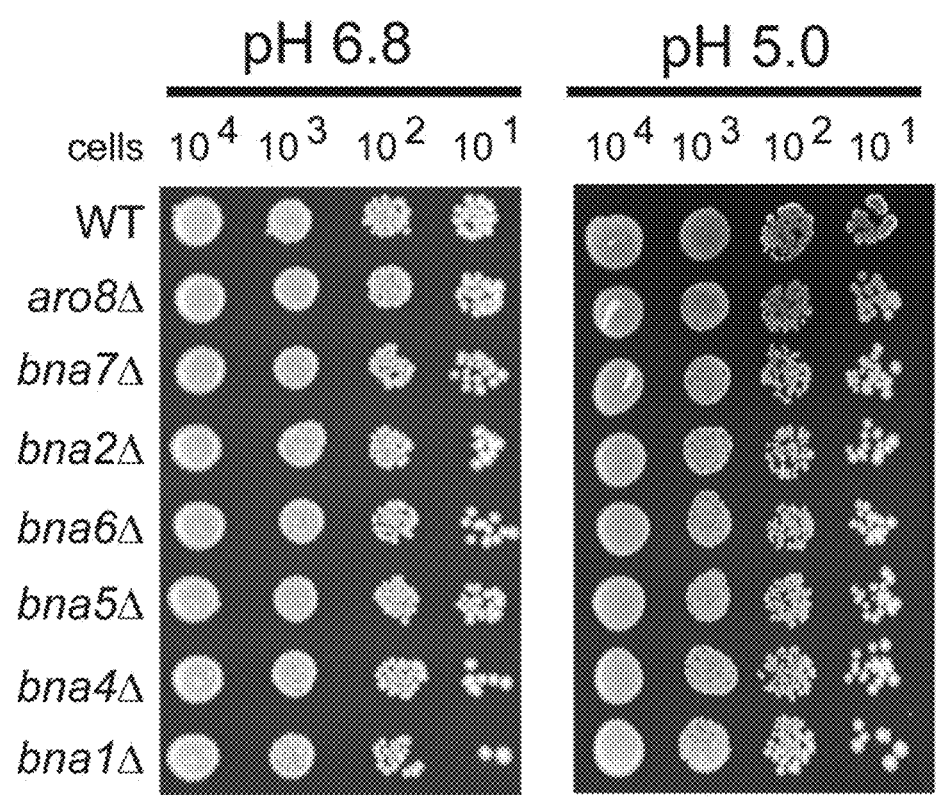
FIG. 3 shows four 10-fold serial dilutions of yeast cultures spotted onto YPD agar plates at pH 6.8 and pH 5.0. The yeast cultures spotted on the agar plates include wild-type (BY4741) as well as the following strains containing deletions of genes encoding proteins in the tryptophan catabolic pathway: aro8Δ (YKB4799), bna7Δ (YKB4649), bna2Δ (YKB4798), bna6Δ (YKB4844), bna5Δ (YKB4845), bna4Δ (YKB4846) and bna1Δ (YKB4729).

As can be seen in FIG. 3, growth was similar for the tryptophan catabolic pathway deletion strains tested at pH 6.8 and 5.0. Without being limited to any particular theory, it is believed that these results show that the resistance of bna7Δ observed in the presence of ferulic acid was not due to acid tolerance.

Experiments were also conducted to determine if deletion of BNA7 could provide protection to 4-hydroxybenzoic acid or coniferyl aldehyde (CA). Wild type (BY4741) and bna7Δ (YKB4649) strains were grown to mid log phase in YPD medium prior to being diluted into fresh medium to an $OD_{600}$ of 0.1. Four 10-fold serial dilutions were spotted onto YPD agar plates containing either no compound (Untreated), 10 mM ferulic acid (FA), 35 mM 4-hydroxybenzoic acid (4-HBA) or 1 mM coniferyl aldehyde (CA). Plates were incubated for 48 hr at 30° C. and images are representative of three biological replicates.

Figure 4:
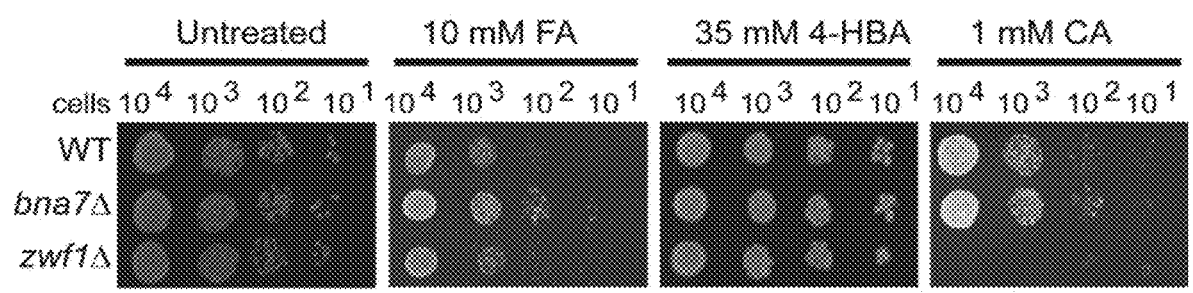
FIG. 4 shows four 10-fold serial dilutions of yeast cultures spotted onto YPD agar plates that were untreated and containing 10 mM ferulic acid, 35 mM 4-hydroxybenzoic acid and 1 mM coniferyl aldehyde. The yeast cultures spotted on the agar plates include wild-type (BY4741) as well as bna7Δ (YKB4649) and zwf1Δ (YKB4794).

As shown in FIG. 4, bna7Δ were resistant to ferulic acid, but not 4-hydroxybenzoic acid or coniferyl alcohol. Without being limiting, it is believed that deletion of BNA7 does not provide protection to 4-hydroxybenzoic acid or coniferyl aldehyde (CA).

Figure 5A:
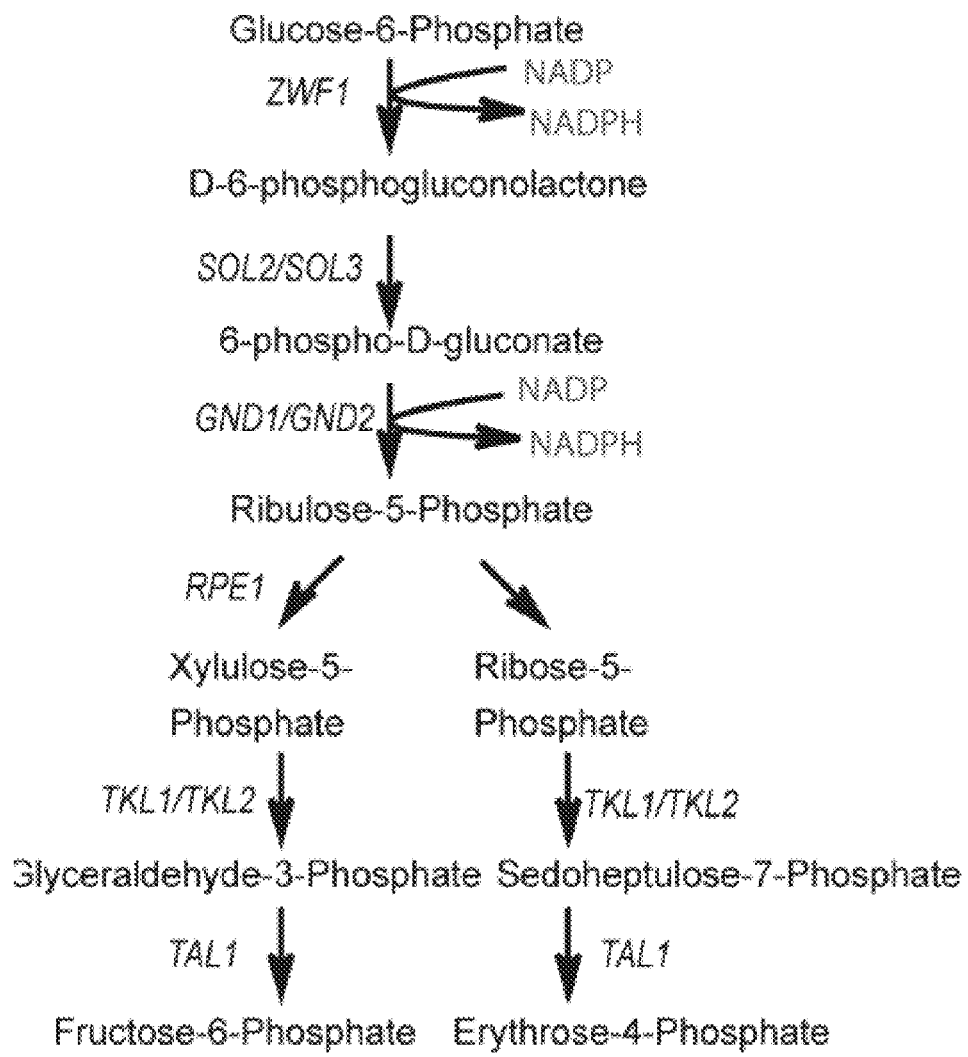
FIG. 5A is a diagram showing the pentose phosphate pathway.

Example 4: Proteins in the Pentose Phosphate Pathway Imrprove Tolerance to Coniferyl Aldehyde The coniferyl aldehyde chemogenomic screen identified three genes that code for enzymes in the pentose phosphate pathway (FIG. 5A), namely ZWF1, TKL1 and RPE1. Strains with deletion of genes encoding proteins in the pentose phosphate pathway were further characterized below.

Figure 5B:
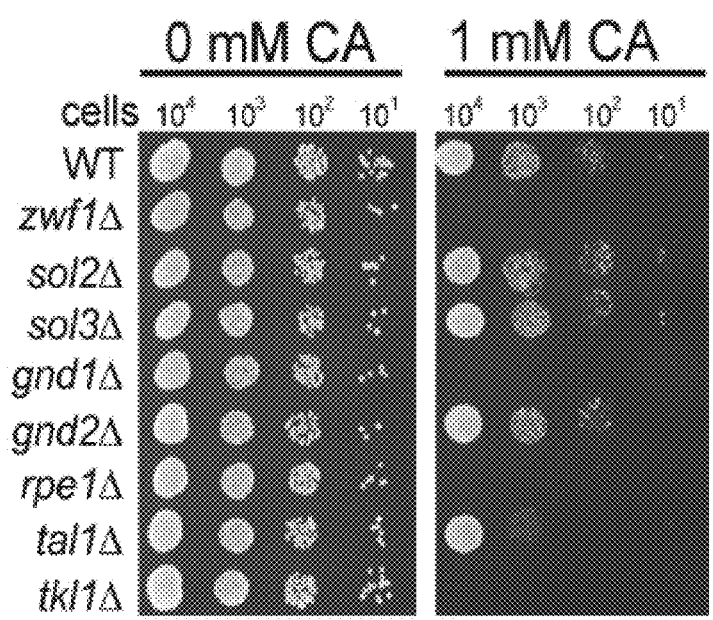
FIG. 5B shows four 10-fold serial dilutions of yeast cultures spotted onto YPD agar plates containing 0 mM coniferyl aldehyde or 1 mM of coniferyl aldehyde. The yeast cultures spotted on the agar plates include wild-type (BY4741) as well as the following strains containing deletions of genes encoded by proteins in the pentose phosphate pathway: zwf1Δ (YKB4794), sol2Δ (YKB4847), sol3Δ (YKB4848), gnd1Δ (YKB4797), gnd2Δ (YKB4850), rpe1Δ (YKB4795), tal1Δ (YKB4851) and tkl1Δ (YKB4796).

Through dot assays, it was determined that deletion of ZWF1, TKL1 and RPE1, along with GND1, displayed a significant growth defect on agar plates containing 1 mM coniferyl aldehyde compared to the wild type strain. Wild type (BY4741) along with zwf1Δ (YKB4794), sol2Δ (YKB4847), sol3Δ (YKB4848), gnd1Δ (YKB4797), gnd2Δ (YKB4850), rpe1Δ (YKB4795), tal1Δ (YKB4851) and tkl1Δ (YKB4796) deletion strains were grown to mid log phase in YPD medium prior to being diluted into fresh medium to an $OD_{600}$ of 0.1. Four 10-fold serial dilutions were spotted onto YPD agar plates containing either 1 mM coniferyl aldehyde (1 mM CA) or no coniferyl aldehyde (0 mM CA). Plates were incubated for 48 hr at 30° C. and images are representative of three biological replicates. The results are shown in FIG. 5B. As can be seen, no growth was observed with zwf1Δ (YKB4794), gnd1Δ (YKB4797), rpe1Δ (YKB4795) and tkl1Δ (YKB4796).

ZWF1 encodes glucose-6-phosphate dehydrogenase, an enzyme which catalyses the rate-limiting step of the pathway and is a major generator of cellular NADPH (Nogae and Johnston, 1990, Gene, 96, 161-169). GND1 encodes a 6-phosphogluconate dehydrogenase and is the third enzyme of the oxidative branch of the pentose phosphate pathway. Moreover, the enzyme is a generator of intracellular NADPH (He et al., BMC Structural Biology. 7, 38-38), together with ZWF1. RPE1 encodes D-ribulose-5-phosphate 3-epimerase (Juhnke et al., 1996, Molecular & General Genetics: MGG, 252, 456-64) and TKL1 encodes a transketolase (Sundstrom et al., 1993, The Journal of Biological Chemistry, 268, 24346-52). In these experiments, no pentose phosphate pathway genes were identified in the ferulic acid or 4-hydroxybenzoic acid chemogenomic screens (see FIG. 1).

In addition, direct tests were conducted to compare the sensitivity of zwf1Δ cells to coniferyl aldehyde, ferulic acid or 4-hydroxybenzoic acid. (The sensitivity of wild-type and bna7Δ to these inhibitors was examined as well as set forth in Example 3).

Wild type (BY4741), bna7Δ (YKB4649) and zwf1Δ (YKB4794) were grown to mid log phase in YPD medium prior to being diluted into fresh medium to an $OD_{600}$ of 0.1. Four 10-fold serial dilutions were spotted onto YPD agar plates containing either no compound (Untreated), 10 mM ferulic acid (FA), 35 mM 4-hydroxybenzoic acid (4-HBA) or 1 mM coniferyl aldehyde (CA). Plates were incubated for 48 hr at 30° C. and images are representative of three biological replicates.

As shown in FIG. 4, the growth of zwf1Δ (YKB4794) on 10 mM ferulic acid (FA) and 35 mM 4-HBA was similar to that of wild-type. Further, there was limited growth of zwf1Δ in the presence of 1 mM of coniferyl aldehyde. Without being limiting, it is believed that Zwf1 reduces the toxicity of coniferyl aldehyde, but not ferulic acid or 4-hydroxybenzoic acid.

Example 5: Phenolic Compounds Induce Reactive Oxygen Species Production in *S. cerevisiae*

Microscopy studies were conducted to determine whether ferulic acid, 4-hydroxybenzoic acid and coniferyl aldehyde induce ROS production in wild-type yeast.

For all microscopy experiments overnight cultures of wild-type yeast grown at 30° C. were re-suspended at an $OD_{600}$ of 0.1 in YPD medium and allowed to reach mid-log phase prior to imaging. Measurement of ROS was performed as previously described (Kennedy et al., 2016, Sci Rep. 6, 19332). Briefly cells were incubated with 10 μM 2',7'-dichlorodihydrofluorescein diacetate ($H_2DCFDA$; Invitrogen cat. #D399) for 15 min in the dark. Cells were washed in sterile PBS to remove traces of the dye after which they were re-suspended in YPD medium alone, or YPD supplemented with either 2 mM coniferyl aldehyde, 10 mM ferulic acid or 50 mM 4-hydroxybenzoic acid or hydrogen peroxide for 1 hour at 30° C.

Live cell imaging was performed by briefly centrifuging the cells (800 g for 2 min), followed by resuspending in a minimal volume of SC medium (67% yeast nitrogen base without amino acids, 0.2% amino acid drop out mix, 2% glucose). An aliquot of 5 μL was spotted onto glass slides and covered with a cover slip prior to imaging. All images were acquired using a Leica DMI 6000 florescent microscope (Leica Microsystems GmbH, Wetzler Germany), equipped with a Sutter DG4 light source (Sutter Instruments, California, USA), Ludl emission filter wheel with Chroma band pass emission filters (Ludl Electronic Products Ltd., NY, USA) and Hamamatsu Orca AG camera (Hamamatsu Photonics, Herrsching am Ammersee, Germany). Images were acquired at 0.2 μm steps across 6 μm using a 63× oil-immersion objective with a 1.4 numerical aperture.

Analysis of $H_2DCFDA$ fluorescence was performed using Velocity Software V4 (Perkin Elmer). Image J software was used to quantify the $H_2DCFDA$ fluorescence signal in cells as described by Schneider et al (Schneider et al., 2012, Nature Methods, 9, 671-675) with a slight modification. Briefly, background fluorescence was subtracted from the images and the total fluorescence of all the cells in the image was measured and divided by the number of cells in the image. The images contained a minimum of 100 cells. The ratio of fluorescence per cell of treated cultures was divided by that of untreated cultures to eliminate background endogenous ROS production.

Figure 6A:
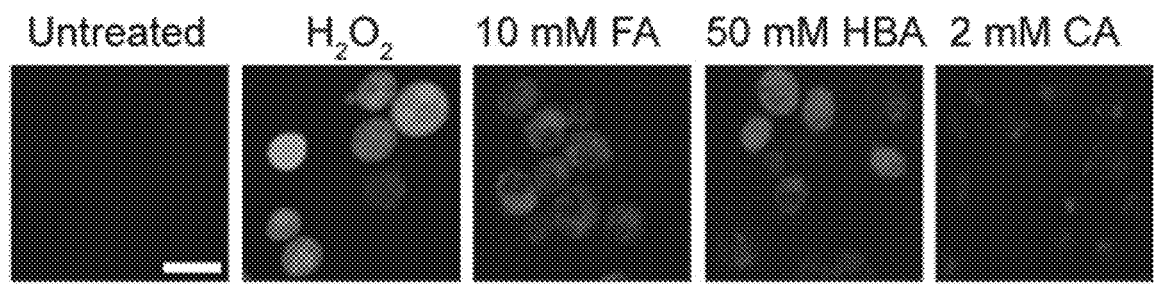
FIG. 6A are microscopy images showing levels of reactive oxygen species (ROS) in wild-type cells in the presence of 10 μM hydrogen peroxide, 10 mM ferulic acid, 50 mM 4-hydroxybenzoic acid and 2 mM coniferyl aldehyde as measured by fluorescence of the dye, 2',7'-dichlorodihydrofluorescein diacetate ($H_2DCFDA$). The cells tested were from wild-type strain BY4741. The scale bar represents 10 μm.

No or limited ROS was detected in untreated cells, while hydrogen peroxide treatment induced the formation of green fluorescence signal throughout the cell (FIG. 6A). The three phenolic compounds also induced ROS formation (FIG. 6A). As seen in FIG. 6A, the ROS produced by ferulic acid and 4-hydroxybenzoic acid was distributed throughout the cell similar to what is seen by hydrogen peroxide treatment. Coniferyl aldehyde-induced ROS formed punctate structures within the cell. Without being limiting, this suggests that coniferyl aldehyde-induced ROS is localized to specific subcellular compartments within the cell and ferulic acid and 4-hydroxybenzoic acid-induced ROS is mainly cytosolic.

Figure 6B:
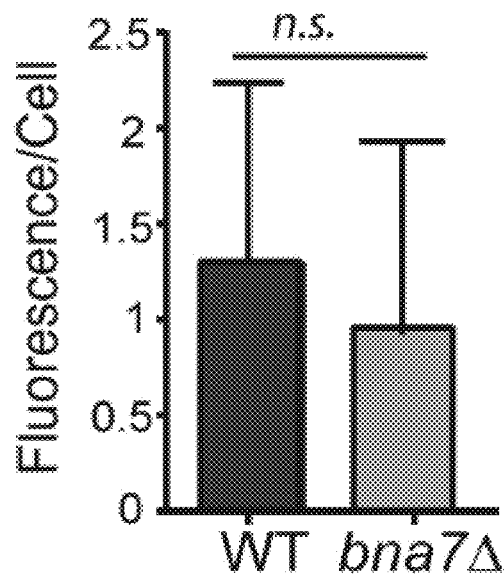
FIG. 6B is a bar graph that shows levels of reactive oxygen species (ROS) in cells in the presence of 2 mM coniferyl aldehyde (CA) as measured by fluorescence/cell after treatment with the dye, $H_2DCFDA$. The cells tested were from wild-type (BY4741) and the deletion strain bna7Δ (YKB4649).

To examine whether deletion of BNA7 confers protection to ferulic acid induced ROS, wild type and bna7Δ cells were exposed to 10 mM ferulic acid for 2 hr and ROS was detected using $H_2DCFDA$ dye followed by visual examination under a fluorescence microscope. Ferulic acid-induced ROS was observed in both the wild-type and the bna7Δ strains (FIG. 6B). Though quantification of the ROS signal indicated a slight reduction of ROS in the bna7Δ strain, this was not statistically significant ($\rho$=0.756). While not wishing to be bound by theory, this suggests that BNA7 deletion had limited impact on the ferulic acid-induced ROS levels at the time point tested.

Figure 6C:
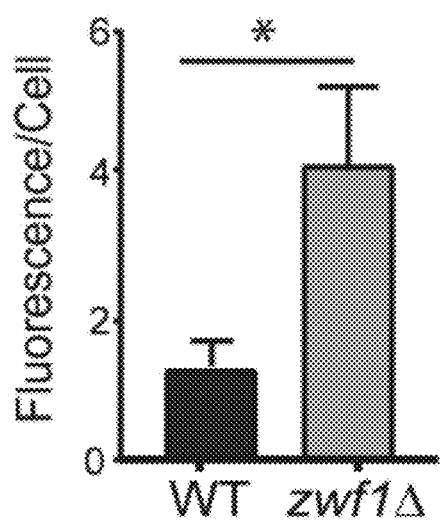
FIG. 6C is a bar graph that shows levels of reactive oxygen species (ROS) in cells in the presence of 2 mM coniferyl aldehyde (CA) as measured by fluorescence/cell after treatment with the dye, $H_2DCFDA$. The cells tested were from wild-type (BY4741) and the deletion strain zwf1Δ (YKB4794).

Next, ROS formation in wild-type and zwf1Δ strains upon exposure to coniferyl aldehyde was examined. Exposure to coniferyl aldehyde induced ROS formation in both wild-type and zwf1Δ strains. As shown in FIG. 6C, the intensity of the ROS signal was higher ($\rho$=0.012) in the zwf1Δ strains. The over two-fold induction of coniferyl aldehyde-induced ROS in the zwf1Δ strain indicate that Zwf1, and likely NADPH production is required to buffer the effect of ROS.

Example 6: Coniferyl Aldehyde-Induced ROS is Localized to the Endoplasmic Reticulum and Mitochondria This example demonstrates that coniferyl aldehyde-induced ROS detected by the assay described in Example 5 (dyeing with $H_2DCFDA$) co-localizes to distinct organelles in the cell.

For co-localization studies, images were obtained as Z-stacks. Co-localization of the fluorescence signals were quantified using the IMARIS software 9.2.1 (Bitplane; http://www.bitplane.com) and a Manders' overlap co-efficient (Manders et al., 1993, Journal of Microscopy. 169, 375-382) was used to evaluate the fraction of RFP pixels (organelle marker) also positive for GFP pixels (ROS marker). The closer the value is to one, the higher the level of co-localization. The analysis was complemented by performing an object-based quantification where the percentage volume of ROS that localized to the mitochondria and endoplasmic reticulum was measured.

Figure 7A:
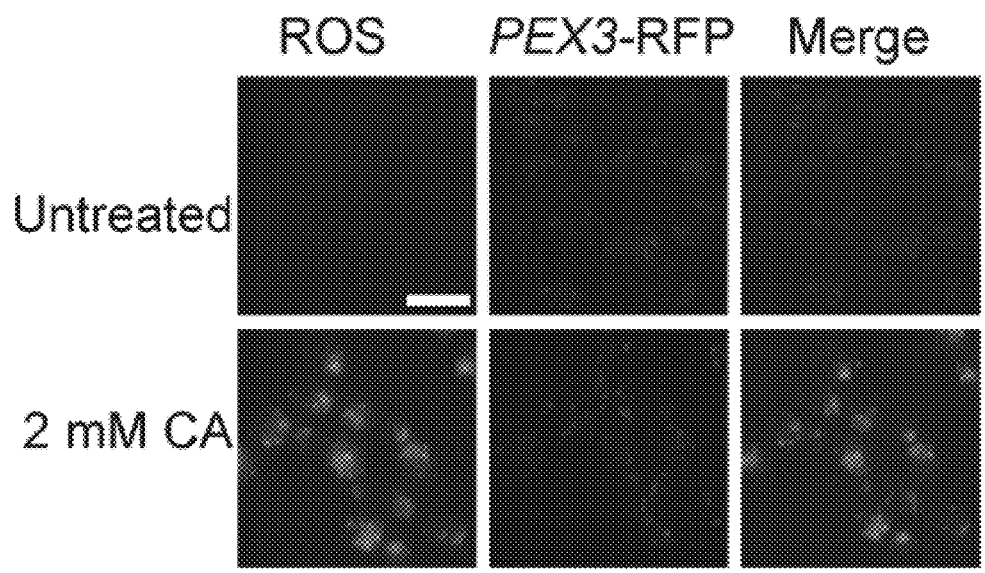
FIG. 7A shows fluorescence microscopy images of wild-type cells treated with 10 μM $H_2DCFDA$ (ROS); wild-type cells treated with 10 μM $H_2DCFDA$ and expressing the endogenously tagged peroxisome marker PEX3-RFP (YKB2500); and merged images. The lower panels show cells that are treated with coniferyl aldehyde (2 mM) and the top panels show untreated cells. The scale bar represents 10 μm.
Figure 7B:
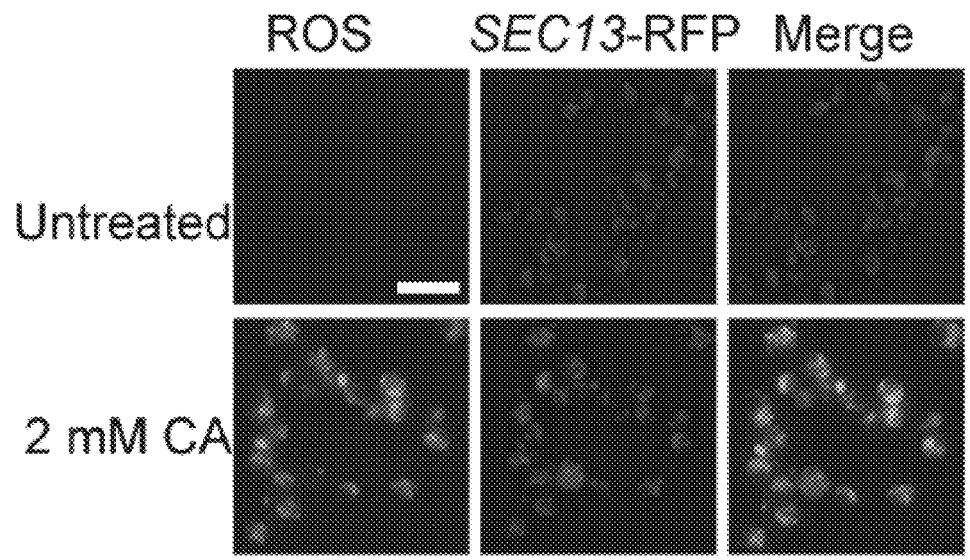
FIG. 7B shows fluorescence microscopy images of wild-type cells treated with 10 μM $H_2DCFDA$ (ROS); wild-type cells treated with 10 μM $H_2DCFDA$ and expressing the endoplasmic reticulum marker SEC13-RFP (YKB4840); and merged images. The lower panels show cells that are treated with coniferyl aldehyde (2 mM) and the top panels show untreated cells. The scale bar represents 10 μm.

It was found that the ROS signal (green) did not overlap with the peroxisome marker (red) suggesting that coniferyl aldehyde-induced ROS did not localize to the peroxisomes (FIG. 7A). However, there was some overlap between the ROS signal and the ER and mitochondria markers (FIG. 7B, C).

Figure 7C:
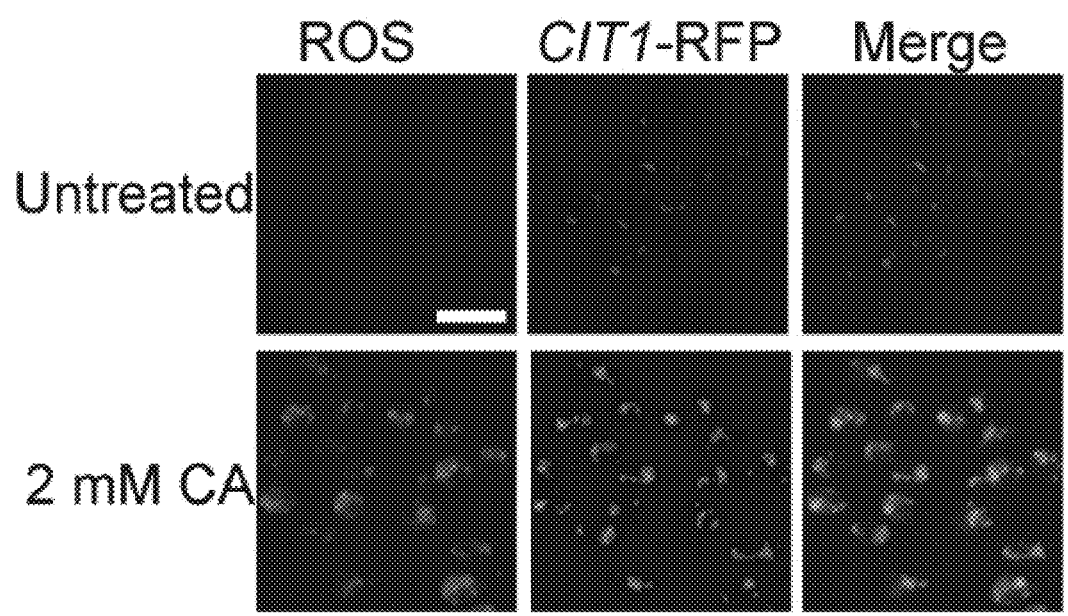
FIG. 7C shows fluorescence microscopy images of wild-type cells treated with 10 μM $H_2DCFDA$ (ROS); wild-type cells treated with 10 μM $H_2DCFDA$ and expressing the mitochondrial marker CIT1-RFP (YKB4840); and merged images. The lower panels show cells that are treated with coniferyl aldehyde (2 mM) and the top panels show untreated cells. The scale bar represents 10 μm.

It was found that the ROS signal partially co-localized with the ER marker SEC13-RFP, (FIG. 7B) with a Manders' overlap co-efficient of 0.13±0.1. The total volume of ROS that localized to the ER was 26.5±12.8%, using the object-based analysis. A higher Manders' overlap co-efficient (0.45±0.04) was detected for ROS co-localization to the mitochondria marker CIT1-RFP (FIG. 7C). By performing an object-based co-localization analysis, the percentage volume of ROS that localized to the mitochondria was quantified as and 54.1±17.29%. Not only did ROS co-localize to the mitochondria, but a high degree of mitochondrial fragmentation was observed after 2 hours of coniferyl aldehyde treatment (FIG. 7C). Without being limiting, these data suggest that coniferyl aldehyde-induced ROS partially accumulates in the ER and mitochondria, the latter of which likely causes mitochondria damage and fragmentation.

Example 7: Coniferyl Aldehyde Treatment Increases Cellular Levels of Zwf1-GFP that Localize to Punctuate Structures Microscopy studies were conducted to determine if Zwf1-GFP localizes to organelles in wild-type cells after coniferyl aldehyde treatment. In addition, total protein levels and Zwf1-GFP levels were determined by western blot analysis after treatment of wild-type cells with coniferyl aldehyde.

For the microscopy studies, wild type cells expressing endogenously tagged Zwf1-GFP (YKB4825) were grown to mid log in YPD, prior to being washed and resuspended in YPD medium (Untreated) or YPD medium containing 2 mM coniferyl aldehyde (CA) for 120 min at 30° C. Images (FIG. 8A) are representative of three independent experiments where a minimum of 100 cells each were imaged. Scale bar represents 10 μm.

Figure 8A:
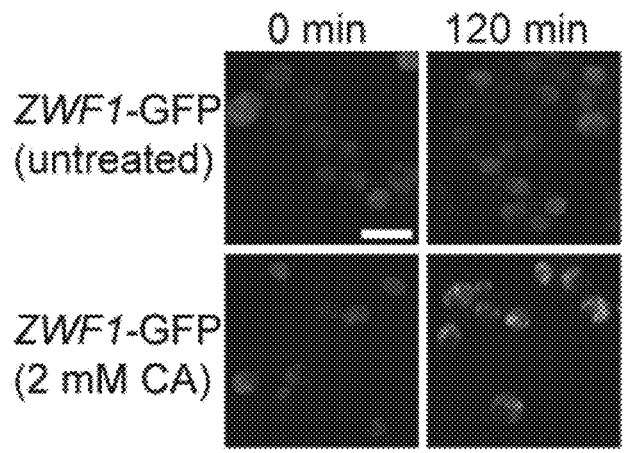
FIG. 8A shows fluorescence microscopy images of wild-type cells having endogenously tagged ZWF1-GFP (YKB4825) treated with 2 mM coniferyl aldehyde (bottom panels) or untreated (top panels). Results are shown at 0 min and 120 min after re-suspension of cells after growth to mid-log phase with YPD with and without coniferyl aldehyde.
Figure 8B:
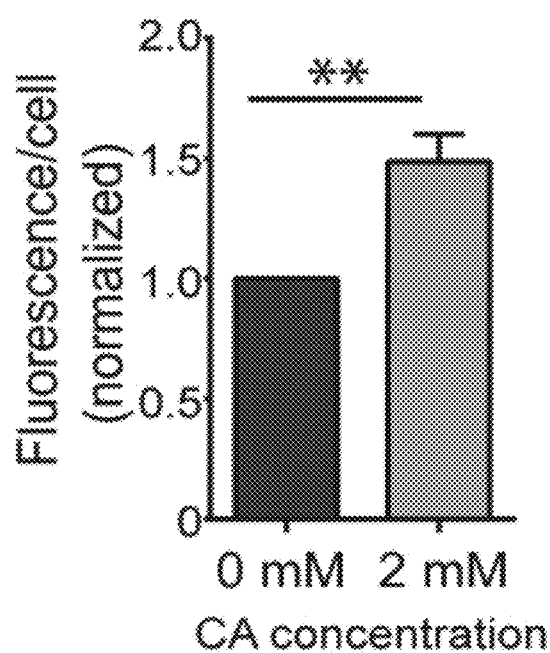
FIG. 8B is a bar graph that quantifies results of fluorescence microscopy as fluorescence/cell for wild-type cells having endogenously tagged ZWF1-GFP (YKB4825) treated with 2 mM coniferyl aldehyde or untreated. Results are from 120 min after re-suspension of cells subsequent to growth to mid log phase with YPD with 2 mM coniferyl aldehyde and without coniferyl aldehyde.

As shown in FIG. 8A, upon 2 hours of coniferyl aldehyde treatment, Zwf1-GFP displayed a punctuate localization and there was a significant increase ($\rho$=9.69E-5) in GFP fluorescence signal/cell (see FIG. 8B).

Protein quantification was carried out by western blots as follows. Overnight cultures of wild type cells were diluted in fresh YPD medium to a final $OD_{600}$ of 0.1. These were grown at 30° C. until they reached the early log phase. Subsequently, coniferyl aldehyde was added to the cultures to a final concentration of 2 mM and the cultures were further incubated for 2 hours. Whole cell extracts (WCE) were obtained by centrifugation of the cells (3000 rpm for 3 min; 4° C.), washing of cell pellet with chilled sterile water and cell lysis using the Trichloroacetic acid (TCA) protocol (Kao and Osley, 2003, Methods. 31,59-66). Equal number of cells was used for the TCA lysis and equal volumes of WCE were used for the quantitative western blot analysis. The WCE was boiled for 10 min and proteins were separated using a TGX stain-free FastCast acrylamide gel (BioRad cat. #161-0181) at 180 V for 2 hr. After the gel electrophoresis, the proteins were transferred onto a nitrocellulose membrane and blocked with 5% non-fat milk powder in Tris-buffered saline solution with Tween 20 for 2 hr. Following the blocking procedure, the nitrocellulose blots were incubated overnight with G6PDH primary antibody (Sigma-Aldrich) after which the membrane was washed (3×10 min) with Tris-buffered saline solution with Tween 20. After washing, the nitrocellulose blots were treated with a secondary antibody (anti-rabbit IgG diluted in the blocking buffer) for 2 hr. In a final step, the nitrocellulose blot was developed with chemiluminiscence reagents (Biorad) and the protein bands were visualized with a ChemiDoc XRS Molecular Imaging system (Biorad). Prior to the protein level quantification, the linear range of the target protein Zwf1 was determined by loading seven 2-fold dilutions of the WCE to obtain a standard curve of protein load versus band intensity of Zwf1. The amount of Zwf1 in the coniferyl aldehyde treated cultures and the control was quantified using the Image Lab software as previously described (Taylor and Posch, 2014, BioMed Research International. 2014, 361590). This was calculated as the ratio of the Zwf1 band intensity to the intensity of bands in the entire lane signal using the TGX Stain-Free Fast Cast (total proteins). The amount of Zwf1 in the coniferyl aldehyde treated cultures was normalized to that of the untreated cultures.

Figure 8C:
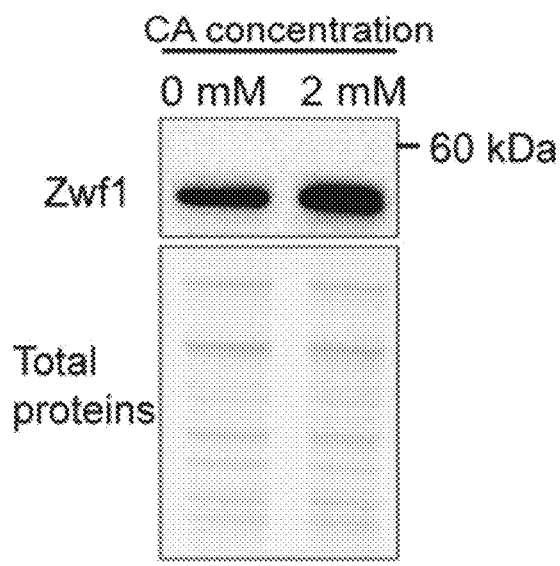
FIG. 8C is a western blot showing Zwf1 protein levels with and without treatment with coniferyl aldehyde (2 mM) in wild-type cells (top panel). The top panel shows Zwf1 protein as measured by anti-Zwf1 antibody. The bottom panel shows total proteins.
Figure 8D:
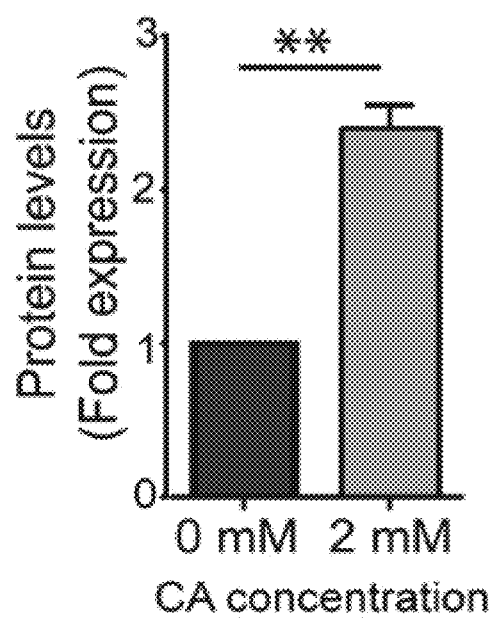
FIG. 8D is a bar graph that quantifies results of the western blot showing protein levels (fold expression) for wild-type cells having endogenously tagged ZWF1-GFP (YKB4825) treated with 2 mM coniferyl aldehyde (CA) or untreated. The graph displays the average of Zwf1 protein levels in cells treated with 2 mM coniferyl aldehyde compared to the untreated (0 mM CA) cells after 2 hrs incubation at 30° C.

The results of the western blot analysis are shown in FIGS. 8C and 8D. In FIG. 8C, Zwf1 protein is depicted by the band in the top panel at 0 mM coniferyl aldehyde and 2 mM coniferyl aldehyde. Exposure to coniferyl aldehyde increased the magnitude of the signal. The bottom band shows total protein. As shown in FIG. 8D, a 1.5 fold increase ($\rho$=0.00176) in Zwf1 protein levels was observed (FIG. 8D) in the presence of 2 mM coniferyl aldehyde. The graph displays the average of Zwf1 protein level in cells treated with 2 mM coniferyl aldehyde compared to the untreated (0 mM CA) cells after 2 hours incubation at 30° C. in three independent experiments. The symbol ** denotes statistical significance at $\rho$<0.005. Error bars represent 1 STD.

Figure 9:
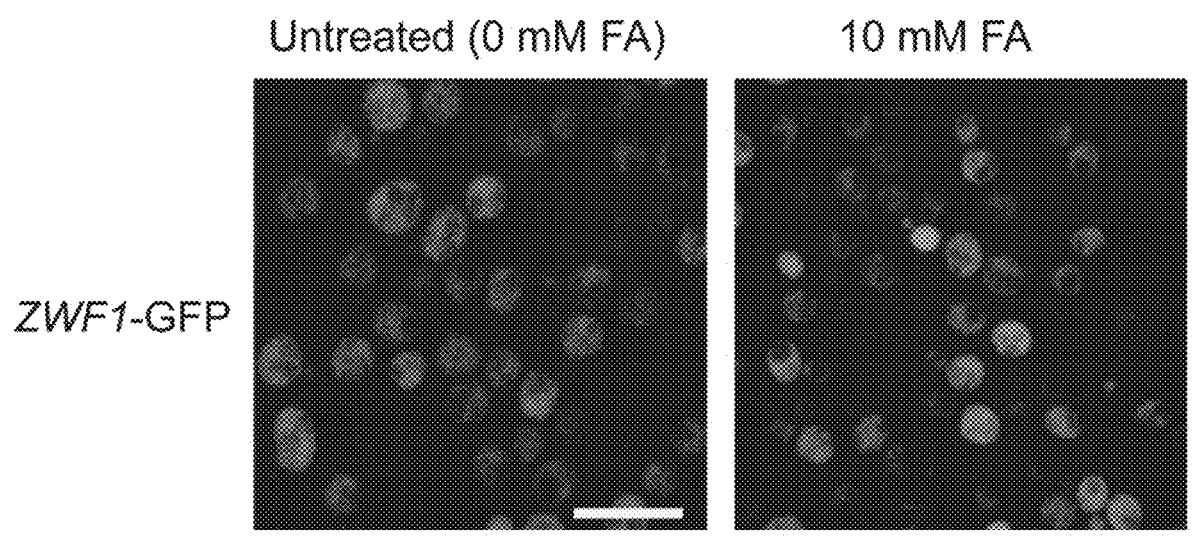
FIG. 9 shows fluorescence microscopy images of wild-type cells expressing endogenously tagged ZWF1-GFP untreated (0 mM ferulic acid) and treated with ferulic acid (10 mM).

There was no increase in Zwf1-GFP fluorescence when the cells were exposed to ferulic acid and 4-hydroxybenzoic acid (FIG. 9).

Figure 10:
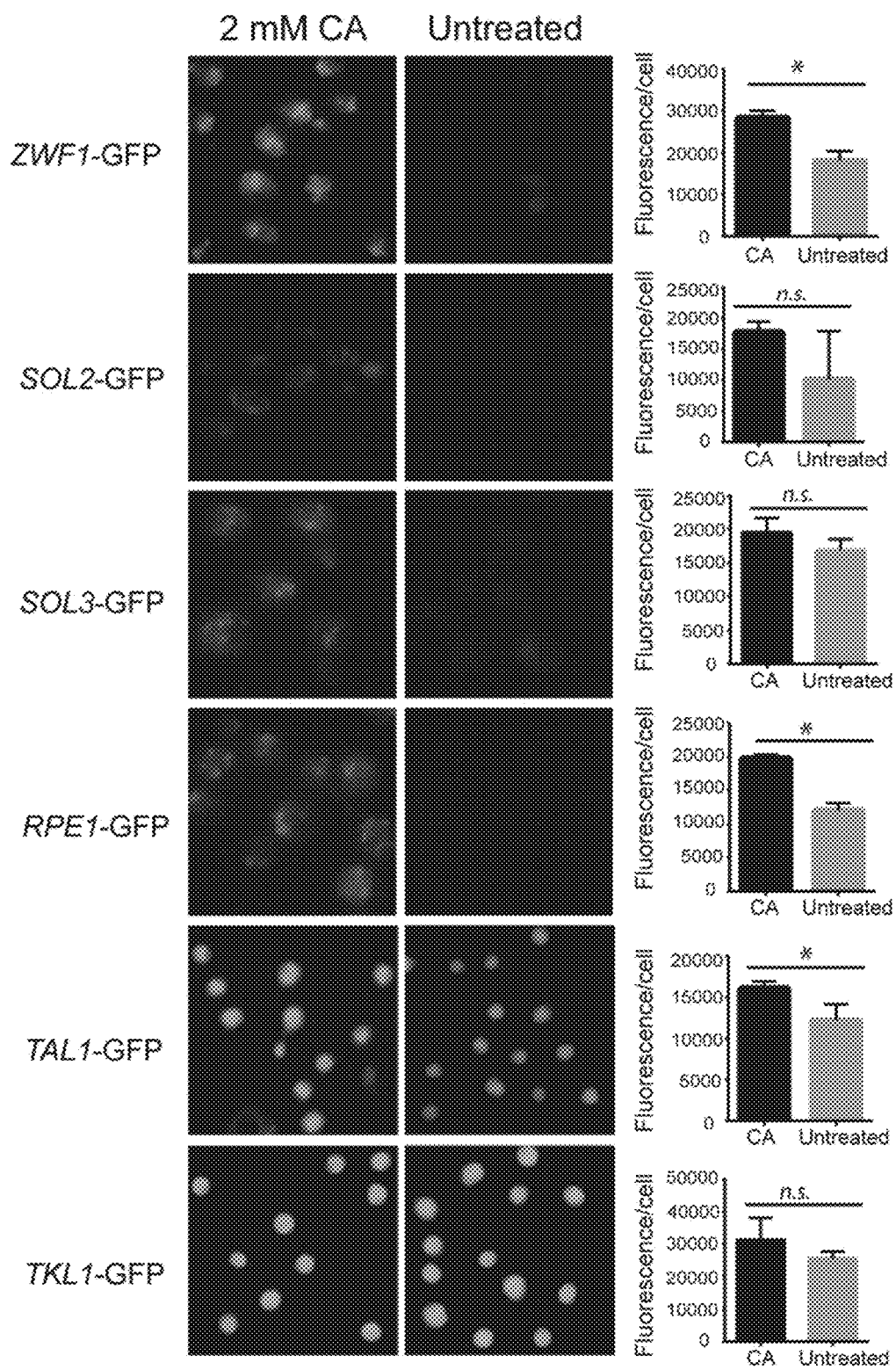
FIG. 10 shows fluorescence microscopy images for wild type cells expressing endogenously tagged proteins in the pentose phosphate pathway including ZWF1-GFP (YKB4825), SOL2-GFP (YKB4841), SOL3-GFP (YKB4842), RPE1-GFP (YKB4824), TAL1-GFP (YKB4852) and TKL1-GFP (YKB 4823) treated with 2 mM coniferyl aldehyde (left panel) or untreated (right panel). Corresponding bar graphs to the right of each image quantify the fluorescence signal (fluorescence/cell) for coniferyl aldehyde treated cells (left bars) and untreated cells (right bars).

For Sol2-GFP, Sol3-GFP and Rpe1-GFP, upon coniferyl aldehyde treatment, a concentration of signal into punctate structures was observed, similar to what we detected for Zwf1-GFP (FIG. 10). Together, the results show that exposure to coniferyl aldehyde drives the induction of a subset of pentose phosphate pathway proteins which are enriched at distinct subcellular locations within the cell.

Example 8: Zwf-1 Co-Localizes to the Mitochondria and ER during Coniferyl Aldehyde Treatment This example demonstrates that Zwf1 localizes to the ER and mitochondria, which are sites of coniferyl aldehyde-induced ROS. This observation supports that localized pools of NADPH could be produced at these locations in the cell to mitigate the toxicity of ROS.

Figure 11A:
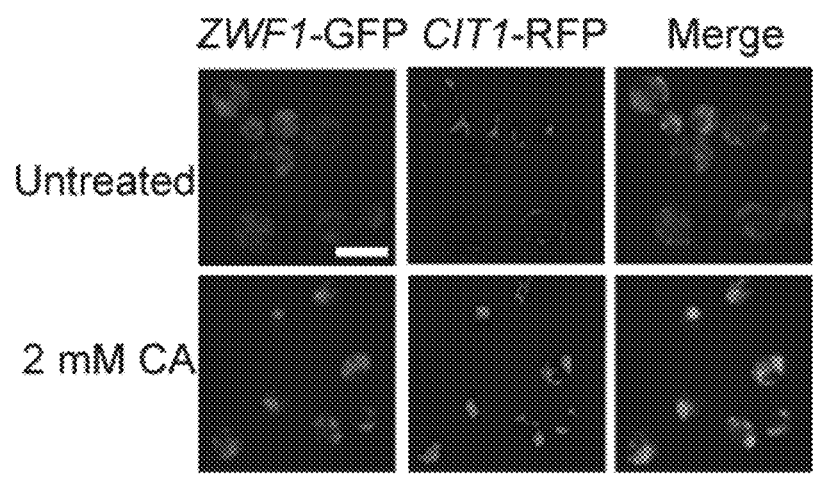
FIG. 11A shows fluorescence microscopy images of wild-type cells expressing endogenously tagged ZWF1-GFP and the mitochondrial marker, CIT1-RFP (YKB4840) and merged images. The top panel shows untreated cells and the bottom panel shows cells treated with coniferyl aldehyde (CA) at 2 mM.
Figure 11B:
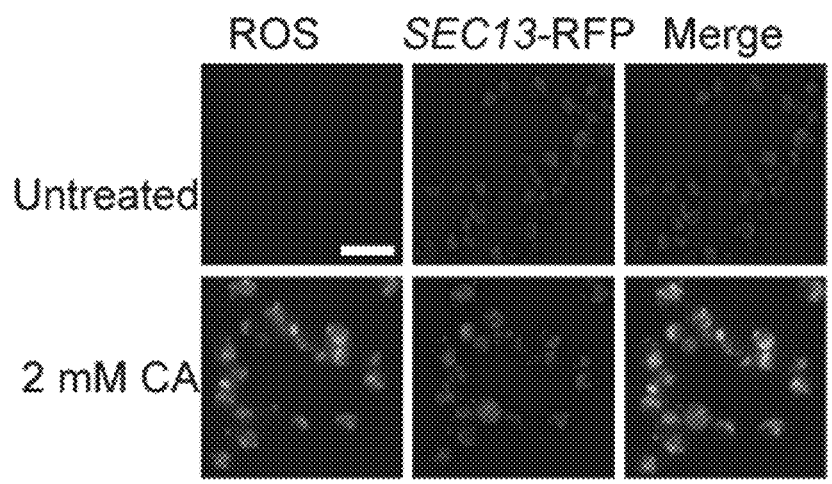
FIG. 11B shows fluorescence microscopy images of wild-type cells expressing endogenously tagged ZWF1-GFP and the endoplasmic reticulum marker, SEC13-GFP (YKB4839) and merged images. The top panel shows cells untreated with coniferyl aldehyde (CA) and the bottom panel shows cells treated with coniferyl aldehyde at 2 mM.

A strain expressing endogenously tagged Zwf1-GFP and either the mitochondrial marker CIT1-RFP or the ER marker SEC13-RFP were imaged as described in Example 5 both before and after 2 hours of treatment with 2 mM coniferyl aldehyde. Zwf1-GFP was found to localize to the mitochondria (Manders' overlap coefficient=0.34±0.07) during coniferyl aldehyde treatment (FIG. 11A). Using the object-based analysis, the percentage volume of Zwf1 localizing to the mitochondria was measured as 47.10±8.04%. Likewise, co-localization of Zwf1-GFP to the ER marker Sec13-RFP was observed, though to a lesser extent, and confirmed by a quantitative analysis using a Mander's overlap co-efficient (0.22±0.07). (FIG. 11B). These results indicate that upon coniferyl aldehyde treatment, Zwf1-GFP interacts with and partially localizes to both the mitochondria and ER, which are sites of coniferyl aldehyde-induced ROS.

Example 9: Characterization of an Industrial Yeast Strain with a BNA7 Deletion

This example demonstrates that the tolerance phenotype conferred by a BNA7 deletion is transferable to other microbial strains under conditions simulating industrial fermentations. As detailed below, an industrial BNA7 deletion mutant exhibited properties that are desirable for the production of a fermentation product on an industrial scale. While ethanol production was examined below, other fermentation products can be produced as well using such deletion strains.

A diploid industrial yeast strain (CEN.PK 113-7D; see Table 1 above) was used to examine the industrial utility of the BNA7 deletion on tolerance to phenolic fermentation inhibitors present in plant hydrolysates. Growth, glucose consumption and ethanol production of the BNA7 deletion strain were compared to a wild-type CEN.PK strain in bioreactors using synthetic corn hydrolysate as the substrate.

To prepare the mutant strain, BNA7 was deleted on both alleles of the diploid strain to obtain a BNA7 deletion mutant, CEN.PK BNA7$^{-/-}$. This strain was characterized and compared to the wild type strain in bioreactors containing 300 mL synthetic corn hydrolysate. Synthetic corn hydrolysate medium (60 g/L glucose, 26 g/L xylose, yeast nitrogen base, 1.3 mM ferulic acid, 2.1 mM p-coumaric acid, 0.197 mM coniferyl aldehyde, 10 µM 4-hydroxybenzoic acid and 0.132 mM vanillin) was prepared as described previously by Sitepu, I. R. et al., 2014, Appl Microbiol Biotechnol, 98, 7645-7657 and Keating et al., 2014, Front Microbiol, 5, 402, each of which is incorporated herein by reference.

The synthetic hydrolysate contained five major phenolic compound inhibitors (ferulic acid, p-coumaric acid, coniferyl aldehyde, 4-hydroxybenzoic acid and vanillin) found in corn hydrolysates (Keating, D. H. et al., Front Microbiol, 5, 402 (2014)) and the tolerance to the inhibitors (measured as an increase in biomass) and glucose consumption under such toxic conditions was determined. Ethanol was measured as a product of fermentation. Since glycerol is a known modulator of yeast stress (see Hohmann, S., Krantz, M. & Nordlander, B. in *Osmosensing and Osmosignaling* (eds. Häussinger, D. & Sies, H. B. T.-M. in E.) 428, 29-45 (Academic Press, 2007), this compound was quantified to eludicate yeast stress.

The growth conditions used in the experiments were as follows. Overnight yeast cultures grown in yeast peptone dextrose (YPD) medium were centrifuged, washed and used to inoculate fresh synthetic corn hydrolysate medium. The cultures were incubated at 30° C. for 4-5 hours until they reached the log phase ($OD_{600}$~0.5-0.6) after which they were used to inoculate 300 mL of synthetic corn hydrolysate medium in 300 mL Applikon™ bioreactors. Fermentations in the bioreactors were carried out at 30° C. and $OD_{600}$ readings were taken every 2 hours (excluding between 8 and 16 hours) using a spectrophotometer.

Aerobic batch fermentation was carried out at 30° C. with the pH maintained at 5.0 with the automatic addition of 2 M potassium hydroxide. The cultures were stirred with an initial agitation of 500 rpm. The stirring was increased over time to ensure that the dissolved oxygen level was maintained above 30% saturation. Samples were taken every two hours for metabolite analysis (excluding between 8 and 16 hours) using high performance liquid chromatography (HPLC) and to measure changes in biomass ($OD_{600}$). Glucose, ethanol and glycerol concentrations in the culture supernatants were quantified using refractive index (RI) and ultraviolet (UV) detectors and an Aminex™ HPX-87H column. The column was eluted with $H_2SO_4$ at a flow rate of 0.6 mL/min.

Figure 12:
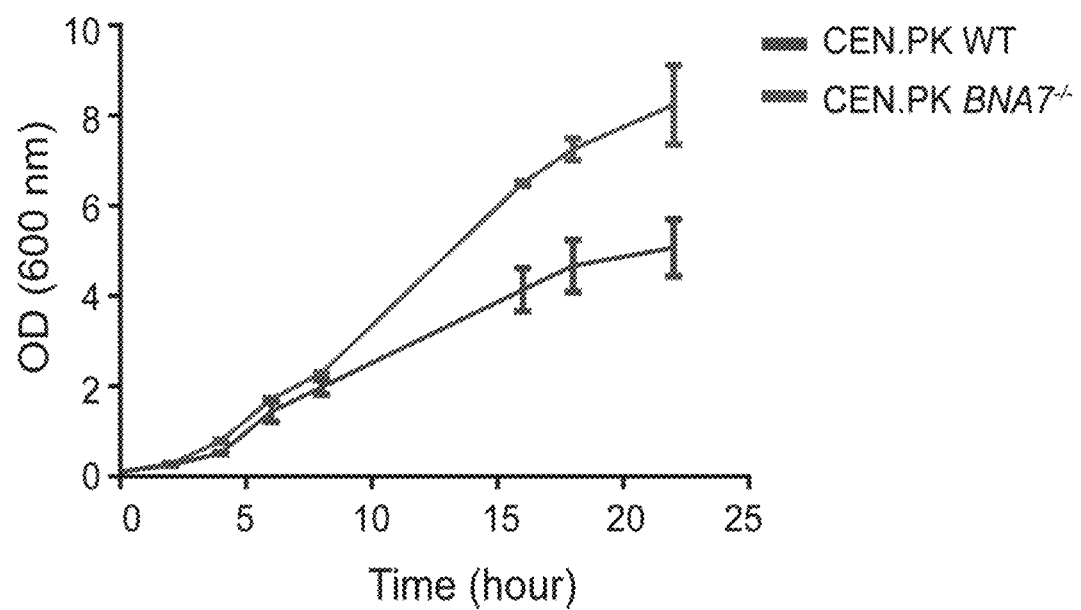
FIG. 12 shows the growth curves of an unmodified wild-type industrial strain CEN.PK 113-70 (bottom curve) and a corresponding CEN.PK BNA7$^{-/-}$ deletion strain (top curve). Growth was determined by measuring biomass ($OD_{600}$) in synthetic corn hydrolysate containing a variety of toxic phenolic fermentation inhibitors (ferulic acid, p-coumaric acid, 4-hydroxybenzoic acid, coniferyl aldehyde and vanillin). The growth curves are an average of duplicate readings (biological replicates).

When grown in the synthetic corn hydrolysate, the engineered industrial yeast strain CEN.PK BNA7$^{-/-}$ grew better than the corresponding wild type CEN.PK strain, suggesting an improvement in tolerance to the phenolic compound mixture in the synthetic corn hydrolysate (FIG. 12).

Figure 13:
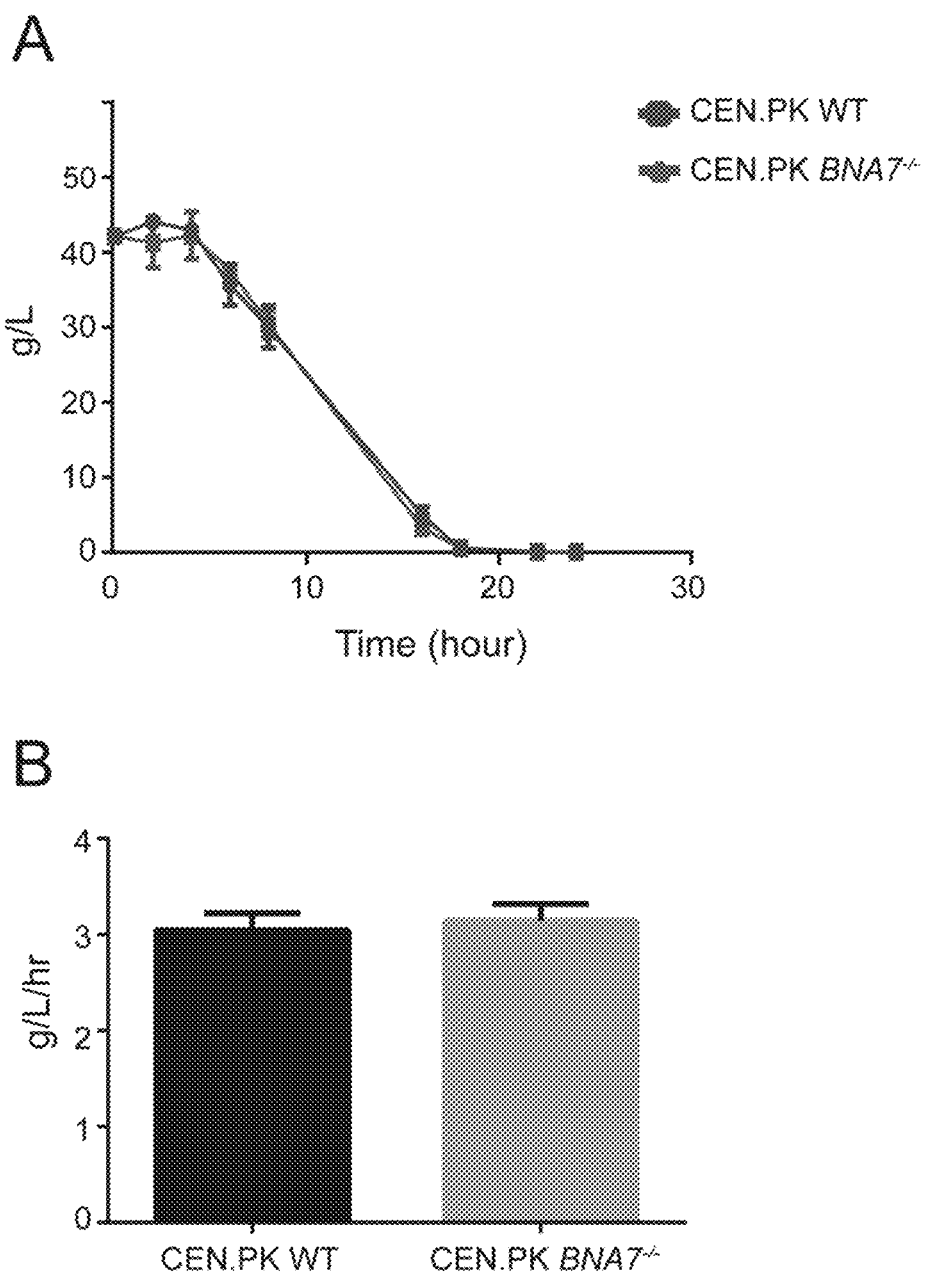
FIG. 13A shows the glucose consumption of the CEN.PK 113-7D wild-type strain (circles) and the CEN.PK BNA7$^{-/-}$ deletion strain (squares). The substrate was synthetic corn hydrolysate containing toxic phenolic fermentation inhibitors (ferulic acid, p-coumaric acid, 4-hydroxybenzoic acid, coniferyl aldehyde and vanillin). The glucose consumption is an average of duplicate readings (biological replicates).
FIG. 13B shows the calculated glucose consumption rates for CEN.PK 113-7D wild-type and the CEN.PK BNA7$^{-/-}$ deletion strain in synthetic corn hydrolysates containing the toxic phenolic fermentation inhibitors noted above. The glucose uptake rates are an average of duplicate readings (biological replicates).

The efficiency of glucose consumption was examined using the mutant CEN.PK deletion strain. Over the course of the fermentation, both the deletion CEN.PK strain and the wild type CEN.PK strain consumed all the glucose in the medium (FIG. 13A). As shown in FIG. 13B, the calculated glucose consumption rate was identical for both wild type CEN.PK and CEN.PK BNA7$^{-/-}$ strains (ρ>0.05).

Figure 14:
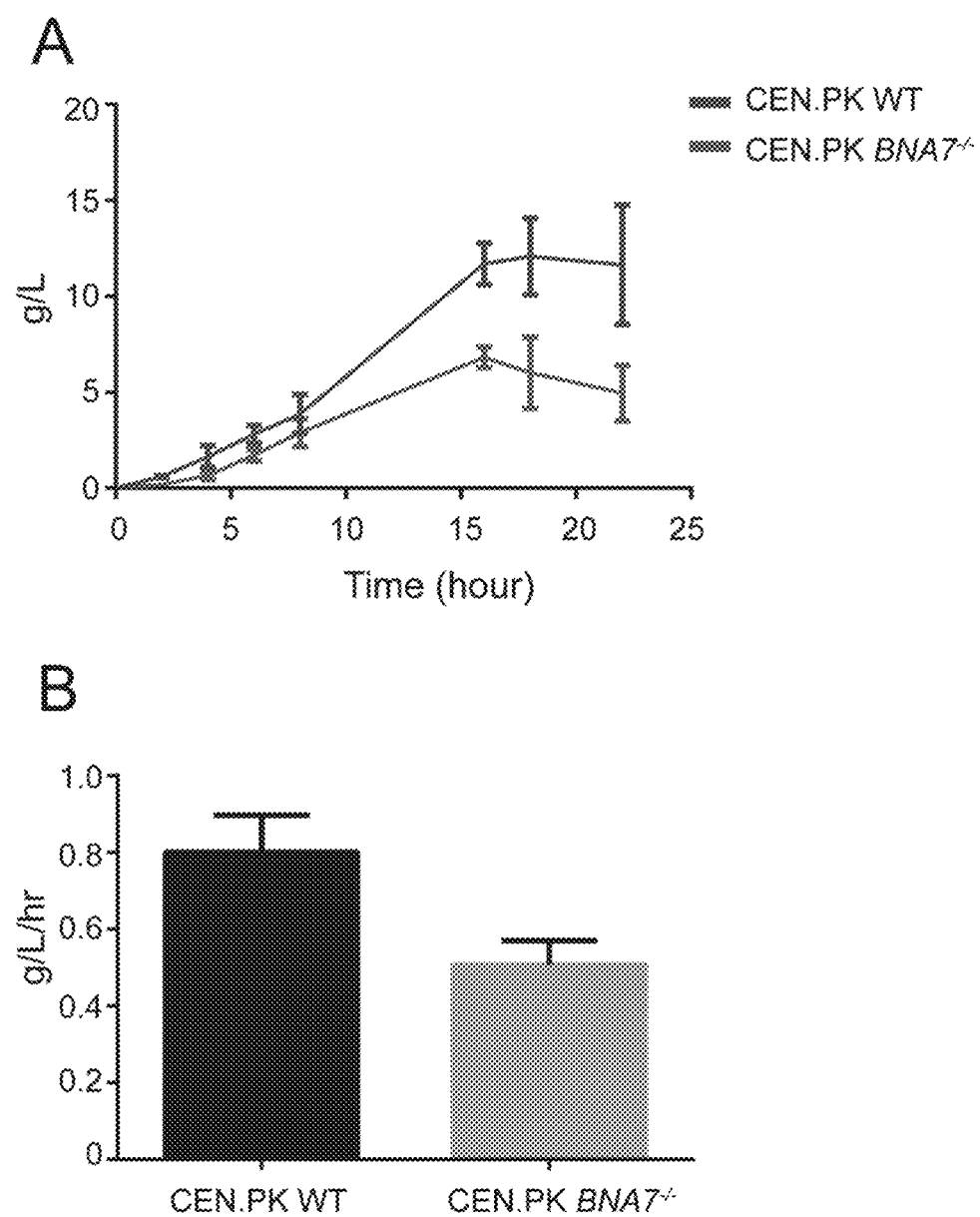
FIG. 14A shows the ethanol produced by the CEN.PK 113-7D wild-type (top curve) and the BNA7$^{-/-}$ deletion strain (bottom curve) over time in synthetic corn hydrolysates containing the toxic phenolic fermentation inhibitors set forth above. The ethanol produced is an average of duplicate readings (biological replicates).
FIG. 14B shows the calculated ethanol production rates of CEN.PK 113-7D wild-type and the BNA7$^{-/-}$ deletion strains using the synthetic corn hydrolysates. The ethanol production rates are an average of duplicate readings (biological replicates).
Figure 15:
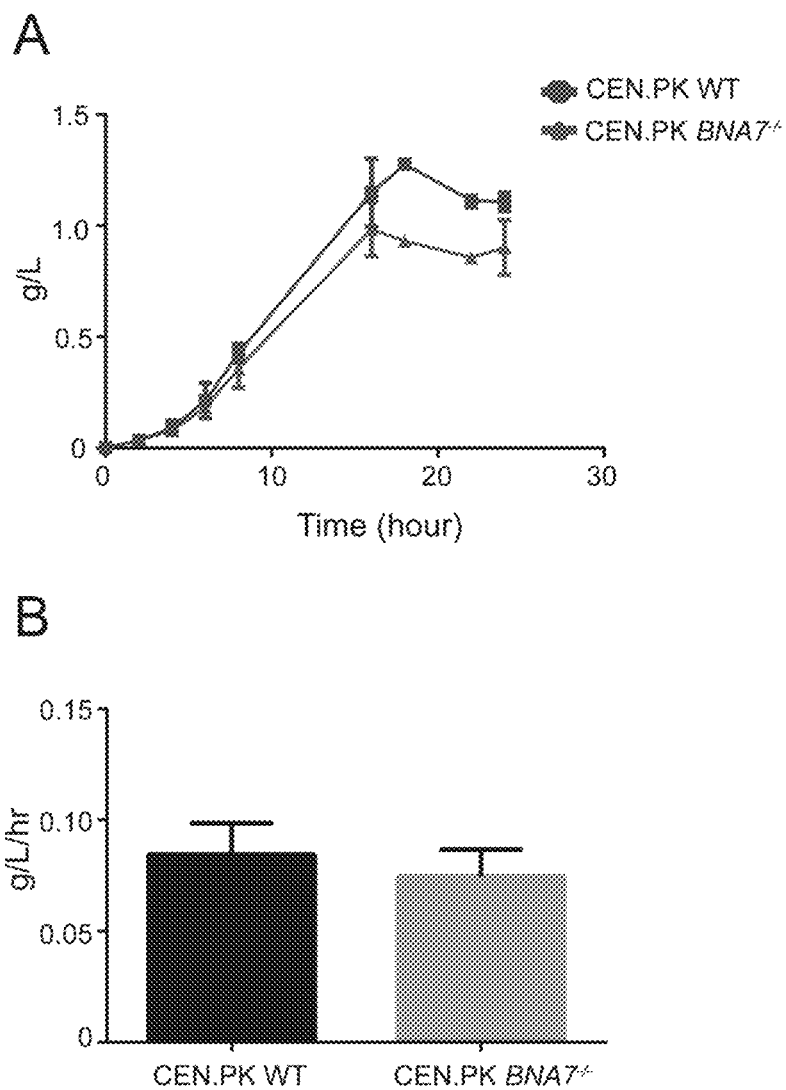
FIG. 15A shows the glycerol production of CEN.PK 113-7D wild-type and the BNA7$^{-/-}$ deletion strains. Glycerol concentration in the supernatants of the bioreactors was quantified by HPLC measurements every two hours over the course of the fermentation in synthetic corn hydrolysates containing toxic phenolic fermentation inhibitors (ferulic acid, p-coumaric acid, 4-hydroxybenzoic acid, coniferyl aldehyde and vanillin). The glycerol produced is an average of duplicate readings (biological replicates).
FIG. 15B shows the calculated glycerol production rate for wild type CEN.PK and CEN.PK BNA7$^{-/-}$ strains using the synthetic corn hydrolysates. The glycerol production rates are an average of duplicate readings (biological replicates).

Subsequently, the amount and rate of ethanol and glycerol production were quantified to determine how the consumed glucose was used apart from growth. The amount and rate of ethanol production was lower in CEN.PK BNA7$^{-/-}$ compared to the wild type CEN.PK strain (FIG. 14A and FIG. 14B). (However, the difference in rates of ethanol production (FIG. 14B) between the two strains was not statistically significant (p>0.05)). Furthermore, both of the CEN.PK wild type and CEN.PK BNA7$^{-/-}$ strains produced glycerol (a by-product of fermentation) at approximately the same rate (FIGS. 15A and 15B). rrrrrrrr Together, these results highlight the fact that the tolerance phenotype conferred by the BNA7 deletion is transferable to other strains and that the method for producing a fermentation product using such strains can be carried out under industrial conditions. Although both the wild type CEN.PK and CEN.PK BNA7$^{-/-}$ strains consumed glucose at the same rate, the CEN.PK BNA7$^{-/-}$ strain channelled a larger portion of the consumed glucose into energy production, growth and tolerance to the phenolic compounds (observed in increased biomass formation). Even though ethanol production was higher in the wild type CEN.PK strain (FIG. 14A), growth of the wild-type strain was significantly limited compared to the CEN.PK BNA7$^{-/-}$ since it could not deal with phenolic compound toxicity.

As growth and biomass yield are a major consideration during the conversion of plant hydrolysates to fuels and fermentation chemicals, CEN.PK BNA7$^{-/-}$ is well suited for such bioprocesses. Particularly, this phenolic tolerant strain can be used as a platform strain to convert plant hydrolysates to non-ethanol biofuels and other value-added chemicals such as vanillin either using ferulic acid or plant hydrolysates as a feedstock for fermentation.

The foregoing description should not be construed as limiting and includes embodiments and equivalents thereof that would be known to those of ordinary skill in the art. A number of embodiments of the invention have been described. Nevertheless, it can be understood that various modifications may be made without departing from the spirit and scope of the invention. Accordingly, other embodiments are within the scope of the following claims.

What is claimed is:

1. A modified yeast strain capable of growing in or fermenting a substrate solution to produce a fermentation product, the solution comprising at least ferulic acid and/or coniferyl aldehyde, the yeast strain having one or more modifications to provide:

(a) a decrease in copy number or expression of a BNA7 gene;

(b) an increase in copy number or expression of one or more pentose phosphate pathway genes; and/or (c) localization of one or more products of the pentose phosphate pathway genes to the mitochondria or endoplasmic reticulum;

said pentose phosphate pathway genes selected from at least one of ZWF1, TKL1, RPE1 and GND1, wherein the copy number or expression of the gene or genes in (a) or (b) are measured relative to a parental yeast strain or a wild-type yeast strain.

2. The modified yeast strain of claim 1, wherein the yeast strain comprises:
 (a) a decrease in copy number or expression of the BNA7 gene; and
 (b) an increase in copy number of the one or more genes involved in the pentose phosphate pathway.

3. The modified yeast strain of claim 1, wherein the yeast strain comprises:
 (a) a decrease in copy number or expression of a BNA7 gene; and
 (b) an increase in copy number of the ZWF1 gene.

4. The modified yeast strain of claim 1, wherein the yeast strain comprises:
 (a) a decrease in copy number or expression of the BNA7 gene; and
 (b) localization of one or more products of the pentose phosphate pathway genes to the mitochondria or endoplasmic reticulum.

5. The modified yeast strain of claim 1, wherein the yeast strain comprises:
 (a) a decrease in copy number or expression of the BNA7 gene; and
 (b) localization of the gene product of ZWF1 to the mitochondria or endoplasmic reticulum.

6. The modified yeast strain of claim 1, wherein the decrease in expression of the BNA7 gene is caused by a deletion or inactivation of the BNA7 gene, or a modification of a regulatory element that controls expression of the BNA7 gene in the genome of the yeast.

7. The modified yeast strain of claim 1, wherein the increase in expression of the one or more genes selected from ZWF1, TKL1, RPE1 or GND1 is caused by an increase in copy number of the one more genes, or a modification of a regulatory element that controls expression of the one or more genes in the genome of the yeast.

8. The modified yeast strain of claim 1, wherein the yeast strain is from the genus of *Saccharomyces, Candida, Pichia,* or *Kluyveromyces*.

9. The modified yeast strain of claim 8, wherein the yeast strain is a *Saccharomyces cerevisiae* strain.

10. The modified yeast strain of claim 1, wherein the yeast strain comprises a nucleotide sequence operatively linked to one or more of the genes of the pentose phosphate pathway, which sequence encodes for an amino acid tag that localizes a gene product of the one or more genes to the mitochondria or endoplasmic reticulum of the cell.

11. The modified yeast strain of claim 10, wherein the nucleotide sequence is operatively linked to the ZWF1 gene so that when the ZWF1 gene is expressed, a resultant gene product, Zwf1, comprises the amino acid tag operatively linked thereto, thereby localizing the Zwf1 gene product to the mitochondria or endoplasmic reticulum of the cell.

12. The modified yeast cell of claim 1, wherein the strain comprises a genetic modification to increase a copy number of the ZWF1 gene.

13. The modified yeast cell of claim 1, wherein the solution in which the yeast cell is capable of growing in or fermenting is a lignocellulosic hydrolysate.

14. A modified microbe having a decrease in copy number or expression of a BNA7 gene and/or an increase in copy number or expression of a ZWF gene relative to a parental or wild-type strain.

15. A method for growing in or fermenting a substrate in a solution comprising a phenolic inhibitor, said method comprising exposing the solution to the modified yeast cell of claim 1.

16. A method for fermenting a substrate in a solution comprising at least ferulic acid and/or coniferyl aldehyde to produce a fermentation product, said method comprising exposing the solution to the yeast strain of claim 1 to produce the fermentation product.

17. The method of claim 16, wherein the solution is a lignocellulosic hydrolysate.

18. The method of claim 16, wherein the ferulic acid and/or coniferyl aldehyde is/are derived from a hydrolysis of a lignocellulosic feedstock.

19. The method of claim 16, wherein the fermentation product is a fuel, a chemical or an intermediate thereof.

20. The method of claim 16, wherein the substrate is a sugar or the ferulic acid.

21. The method of claim 19, wherein the chemical is vanillin.

22. A method for growing in or fermenting a substrate in a solution comprising a phenolic inhibitor, said method comprising exposing the solution to the modified microbe of claim 14.

23. A method for fermenting a substrate in a solution comprising at least ferulic acid and/or coniferyl aldehyde to produce a fermentation product, said method comprising exposing the solution to the modified microbe of claim 14 to produce the fermentation product.

* * * * *